US008835493B2

(12) United States Patent
Ahn et al.

(10) Patent No.: US 8,835,493 B2
(45) Date of Patent: Sep. 16, 2014

(54) OLIGO-BENZAMIDE COMPOUNDS FOR USE IN TREATING CANCERS

(71) Applicant: The Board of Regents of the University of Texas System, Austin, TX (US)

(72) Inventors: Jung-Mo Ahn, Plano, TX (US); Ratna K. Vadlamudi, San Antonio, TX (US); Ganesh Raj, Plano, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/683,979

(22) Filed: Nov. 21, 2012

(65) Prior Publication Data

US 2013/0184345 A1    Jul. 18, 2013

Related U.S. Application Data

(60) Provisional application No. 61/563,437, filed on Nov. 23, 2011, provisional application No. 61/664,394, filed on Jun. 26, 2012.

(51) Int. Cl.
    *A61K 31/21*  (2006.01)
(52) U.S. Cl.
    USPC ............................ 514/510; 514/563; 560/45
(58) Field of Classification Search
    USPC ...................... 560/45; 514/510, 563
    See application file for complete search history.

(56) References Cited

U.S. PATENT DOCUMENTS

| 5,212,203 | A | 5/1993 | Shroot et al. | 514/617 |
|---|---|---|---|---|
| 5,929,114 | A | 7/1999 | Domagala et al. | 514/562 |
| 7,217,720 | B2 | 5/2007 | Meissner et al. | 514/284 |
| 7,906,624 | B2 | 3/2011 | Green et al. | 530/387.3 |
| 8,236,983 | B2 | 8/2012 | Ahn | 562/453 |
| 2005/0261346 | A1 | 11/2005 | Zhu et al. | 514/332 |
| 2007/0248535 | A1 | 10/2007 | Buttyan et al. | 424/1.49 |
| 2009/0012141 | A1 | 1/2009 | Ahn | 514/400 |
| 2009/0275519 | A1 | 11/2009 | Nash et al. | 514/1.1 |
| 2010/0069333 | A1 | 3/2010 | Kahn | 514/80 |
| 2010/0125055 | A1 | 5/2010 | Kufe et al. | 514/13 |
| 2010/0178324 | A1* | 7/2010 | Ahn | 424/450 |
| 2010/0317570 | A1 | 12/2010 | Ahn et al. | 514/4.8 |
| 2013/0011465 | A1 | 1/2013 | Ahn | 424/450 |
| 2013/0150442 | A1 | 6/2013 | Ahn et al. | 514/537 |

FOREIGN PATENT DOCUMENTS

| WO | WO 2008/112938 | 9/2008 |
|---|---|---|
| WO | WO 2008/112939 | 9/2008 |
| WO | WO 2008/112941 | 9/2008 |
| WO | WO 2010/088498 | 8/2010 |
| WO | WO 2011/050353 | 4/2011 |
| WO | WO 2011/150360 | 12/2011 |

OTHER PUBLICATIONS

Adams et al., "Life-or-death decisions by the Bcl-2 protein family," *Trends Biochem. Sci*, 26:61-66, 2001.
Ahn et al., "A new approach to search the bioactive conformation of glucagon: positional cyclization scanning," *J. Med. Chem.*, 44:3109-3116, 2001.
Ahn et al., "Development of potent truncated glucagon antagonists," *J. Med. Chem.*, 44:1372-1379, 2001.
Ahn et al., "Facile synthesis of benzamides to mimic an α-helix," *Tetrahedron Letters*, 48:3543-3547, 2007.
Ahn et al., "Peptidomimetics and peptide backbone modifications," *Mini-Reviews in Medicinal Chemistry*, 2:463-473, 2002.
Bulotta et al., "A cultured pancreatic ductal cells undergo cell cycle re-distribution and beta-cell-like differentiation in response to glucagon-like peptide-1," *J. Mol. Endocrinol.*, 29:347-360, 2002.
Burgess et al., "Solid-phase syntheses of β-turn analogues to mimic or disrupt protein-protein interactions," *Acc. Chem. Res.*, 24:826-835, 2001.
Cavaghan et al., "Interactions between insulin resistance and insulin secretion in the development of glucose intolerance," *J. Clin. Invest.*, 106:329-333, 2000.
Chang et al., "Substituted imidazoles as glucagon receptor antagonists," *Bioorg. Med. Chem. Lett.*, 11:2549-2553, 2001.
Chapuis et al., "Shorter puromycin analog synthesis by means of an efficient Staudinger-Vilarrasa coupling," *Tetrahedron*, 62:12108-12115, 2006.
Chen et al., "A nonpeptidie agonist of glucagon-like peptide 1 receptors with efficacy in diabetic db/db mice," *Proc. Natl. Acad. Sci. USA*, 104:943-948, 2007.
Chittenden et al, "A conserved domain in Bak, distinct from BH1 and BH2, mediates cell death and protein binding functions," *EMBO J.*, 14:5589-5596, 1995.
Cochran, "Antagonists of protein-protein interactions," *Chem. Biol.*, 7:R85-R94, 2000.
Database CAPLUS on STN, Acc. No. 2007:1424768, Plante et al., *Organic & Bimolecular Chemistry*, 6(1):138-146, 2008, (Abstract).
Defronso et al.,"Effects of exenatide (exendin-4) on glycemic control and weight over 30 weeks in metformin-treated patients with type 2 diabetes," *Diabetes Care*, 28:1092-1100, 2005.
Dehm, et 01, "Selective role of an NH2-terminal WxxLF motif for aberrant androgen receptor activation in androgen depletion independent prostate cancer cells," *Cancer Res.*, 67:10067-77, 2007.
Drucker et al., "The incretin system: glucagon-like peptide-1 receptor agonists and dipeptidyl peptidase-4 inhibitors in type 2 diabetes," *Lancet*, 368:1696-1705, 2006.
Edwards et al, "Exendin-4 reduces fasting and postprandial glucose and decreases energy intake in healthy volunteers," *Am. J. Physiol. Endocrinol. Metab*, 281:E155-E161, 2001.
Egan et al.,"GLP-1 receptor antagonists are growth and differentiation factors for pancreatic islet beta cells," *Diabetes/Metab. Res. Rev.*, 19:115-123, 2003.
Elbronds et al., "Pharmacokinetics, pharmacodynamics, safety, and tolerability of a single-dose of NN2211, a long-acting glucagon-like peptide 1 derivative, in healthy male subjects," *Diabetes Care*, 25:1398-1404, 2002.

(Continued)

*Primary Examiner* — Rei-tsang Shiao
(74) *Attorney, Agent, or Firm* — Parker Highlander, PLLC

(57) ABSTRACT

The present invention provides bis- and tris-benzamide compounds in the treatment of breast, brain and ovarian cancers.

45 Claims, 10 Drawing Sheets

(56) References Cited

OTHER PUBLICATIONS

Ernst at al., "Design and application of an α-helixmimetic scaffold based on an oligoamide-foldamer strategy: antagonism of the Bak BH3/Bcl-xL complex," *Angew. Chem. Int. Ed.*, 42:535-539, 2003.
Gunther, et al , "Alternative inhibition of androgen receptor signaling: peptidomimetic pyrimidines as direct androgen receptor/coactivator disruptors," *ACS Chem. Biol.*, 4:435-40, 2009.
Hoare et al., "Mechanisms of peptide and nonpepetide ligand binding to class B G-proteincoupled receptors," *Drug Discovery Today*,10:417-427, 2005.
Hruby et al., "Design in topographical space of peptide and peptidomimetic ligands that affect behavior. A chemist's glimpse at the mind—body problem," *Acc. Chem. Res.*, 34(5):389-397, 2001.
Jacoby et al, "Biphenyls as potential mimetics of protein α-helix," *Bioorg. Med. Chem. Lett.*, 12:891-893, 2002.
Knudsen et al., "Glucagon-like peptide-1: the basis of a new class of treatment for type 2 diabetes," *J. Med. Chem.*, 47:4128-4134, 2004.
Knudsen et al., "Small-molecule agonists for the glucagon-like peptide 1 receptor;" *Proc. Natl. Acad. Set. U.S.A.*, 104:937-942, 2007.
Kolterman et al.,"Synehetic exendin-4 (exenatide) significantly reduces postprandial and fasting plasma glucose in subjects with type 2 diabetes," *J. Clin. Endocrinol. Metab.*, 88:3082-3089, 2003.
Konig et al.,"Solid-phase synthesis of oligo(p-benzamide) foldamers,"*Organic Letters*, 8;1819-1822, 2006.
Konig et al.,"Supramolecular PEG-co-Oligo(p-benzamide)s prepared on a peptide synthezier," *J. Am. Chem. Soc.*, 129:704-708, 2007. Published on Web Dec. 23, 2006.
Kussie et al., "Structure of the MDM2 oncoprotein bound to the p53 tumor suppressor transactivation domain," *Science*, 274:948-953, 1996.
Kutzki et al., "Development of a potent Bcl-xL antagonist based on α-helix mimicry," *J. Am. Chem. Soc.*, 124:11838-11839, 2002.
Ling et al., "Identification of alkylidene hydrazides as glucagon receptor antagonists," *J. Med. Chem.*, 44:3141-3149, 2001.
Madsen et al., "Optimization of alkylidene hydrazide based human glucagon receptor antagonists. Discovery of the highly potent and orally available 3-cyano-4-hydroxybenzoic acid [1-(2,3,5,6-tetramethylbenzl)-1H-indol-4-ylmethylene]hydrazide," *J. Med. Chem.*, 45:5755-5775, 2002.
Mahato et al., "Emerging trends in oral delivery of peptide and protein drugs," *Critical Reviews in Therapeutic Drug Carrier Systems*, 20:153-214, 2003.
Marshall, et al. "A hierarchical approach to peptidomimetic design," *Tetrahedron*, 49:3547-3558, 1993.
Matias, at al., "Structural evidence for ligand specificity in the binding domain of the human androgen receptor" *J. Bio. Chem.*, 275:26164-71, 2000.
Murphy, "Nonpeptidic glucagon-like peptide I receptor agonists: A magic bullet for diabetes," *Proc. Natl. Acad. Sci. U.S.A.*, 104:689-690, 2007.
Neidigh at al., "Exendin-4 and glucagon-likepeptide-1: NMR structural comparisons in the solution and micelle-associated states," *Biochemistry*, 40:13188-13200, 2001.
Office Action issued in U.S. Appl. No. 12/048,197, mailed Jan. 14, 2013.
Office Communication issued in U.S. Appl. No. 12/353,173, dated Jan. 11, 2012.
Office Communication issued in U.S. Appl. No. 12/353,173, dated Jun. 23, 2011.
Office Communication issued in U.S. Appl. No. 12/353,173, dated Mar. 24, 2011.
Office Communication issued in U.S. Appl. No. 12/048,197, dated May 9, 2012.
Office Communication issued in U.S. Appl. No. 12/048,197 dated Mar. 23, 2012.
Office Communication issued in U.S. Appl. No. 12/048,197, dated Feb. 23, 2012.
Office Communication issued in U.S. Appl. No. 12/048,197, dated Jul. 6, 2011.
Office Communication issued in U.S. Appl. No. 12/048,197, dated Sep. 22, 2010.
Office Communication issued in U.S. Appl. No. 12/048,197, dated Jul. 12, 2010.
Oguri et al., "Design and synthesis of a trans-fused polycyclic ether skeleton as an a-helix mimetic scaffold," *Tetrahedron Lett.*, 46:2179-2183, 2005.
Orner et al., "Towards proteomimetics: Terphenyl derivatives as structural and functional mimics of extended regions of an α-helix,"*J. Am. Chem. Soc.*, 123:5382-5383, 2001.
PCT International Search Report and Written Opinion, issued in Application No. PCT/US2012/066212, dated Mar. 1, 2013.
PCT International Search Report and Written Opinion, issued in Application No. PCT/US2012/066228, dated Feb. 8, 2013.
PCT International Search Report and Written Opinion, issued in Application No. PCT/US2011/038395, dated Sep. 13, 2011.
PCT International Search Report and Written Opinion issued in International Application No. PCT/US2010/020898, dated Aug. 20, 2010.
PCT International Search Report and Written Opinion issued in International Application No. PCT/US2008/056920, dated Aug. 1, 2008.
PCT International Search Report and Written Opinion issued in International Application No. PCT/US2008/056918, dated Sep. 10, 2008.
Peczuh et al., "Peptide and protein recognition by designed molecules," *Chem Rev. . . .* , 100:2479-2494, 2000.
Perry et al., "The glucagon-like peptides: a double-edged therapeutic sword," *Trends Pharmacol. Sci.*, 24:377-383, 2003.
Plante et al., "Synthesis of functionalised aromatic olicamide rods," *Organic & Biomolecular Chemistry*, 6:138-146, 2008.
Rickard et al., "Intermittend treatment with parathyroid hormone (PTH) as well as a non-petide small molecule agonist of the PTH1 receptor inhibits adipocyte differentiation in human bone marrow stromal cells," *Bone*, 39:1361-1372, 2006.
Runge et al., Different domains of the glucagon and glucagon-like peptide-1 receptors provide the critical determinants of ligand selectivity, *Br. J. Pharmacol.*, 138:787-794, 2003.
Saragoi et al., "Synthetic α-helix mimetics as agonists and antagonists of islet amyloid polypeptide aggregation," *Angewandte Chemie*, 49:736-739, 2010.
Sattler et al., "Structure of Bcl-xL-Bak peptide complex: Recognition between regulators of apoptosis," *Science*, 275:983-986, 1997.
Souers et al., "β-Turn mimetic library synthesis: scaffolds and applications." *Tetrahedron*, 57:7431-7448, 2001.
Stoffers et al., "Insulinotropics glucagon-like peptide 1 agonists stimulate expression of homeodomain protein IDX-1 and increase islet size in mouse pancreas," *Diabetes*, 49:741-749, 2000.
Tanatani et al., "Helical structures of N-alkylated poly(p-benzamide)s," *J. Am. Chem. Soc.*, 127:8553-8561, 2005.
Tibaduiza et al., "A small molecule ligand of the glucagon-like peptide 1 receptor targets its amino-terminal hormone binding domain," *J. Biol. Chem.*, 276:37787-37793, 2001.
Toft-Nielsen et al., "Determinants of the effectiveness of glucagon-like peptide-1 in type 2 diabetes," *J. Clin. Endocrinol. Metab.*, 86:3853-3860, 2001.
Vilsboll et al., "No reactive hypoglycaemia in type 2 diabetic patients after subcutaneous administration of GLP-1 and intravenous glucose," *Diabetic Med.*, 18:144-149, 2001.
Walensky of al., "Activation of apoptosis in vivo by a hydrocarbon-stapled BH3 helix," *Science*, 305:1466-1470, 2004.
Yin et al., "Terephthalamide derivatives as mimetics of helical peptides: Disruption of the Bcl-xL/Bak interaction," *J. Am. Chem. Soc.*, 127:5463-5468, 2005.
Yin et al., "Terphenyl-based Bak BH3 α-helical proteomimetics as low-molecular-weight antagonists of Bcl-xL," *J. Am. Chem. Soc.*, 127:10191-10196, 2005.
Yin et al., "Terphenyl-based helical mimetics that disrupt the p53/HDM2 interaction," *Angew. Chem. Int. Ed.*, 44:2704-2707, 2005.

(56) References Cited

OTHER PUBLICATIONS

Zander et al., "Effect of 6-week course of glucagon-like peptide 1 on glycaemic control, insulin sensitivity, and beta-cell function in type 2 diabetes: a parallel-group study," *Lancet*, 359:824-830, 2002.
Zhang et al., "New approaches in the treatment of type 2 diabetes," *Curr. Opin. Chem. Biol.*, 4:461-467, 2000.
Office Communication issued in U.S. Appl. No. 13/559,388, dated Nov. 7, 2012.
Office Communication issued in U.S. Appl. No. 13/559,388, dated May 2, 2013.
Office Communication issued in U.S. Appl. No. 13/683,932, dated Jul. 10, 2013.

\* cited by examiner

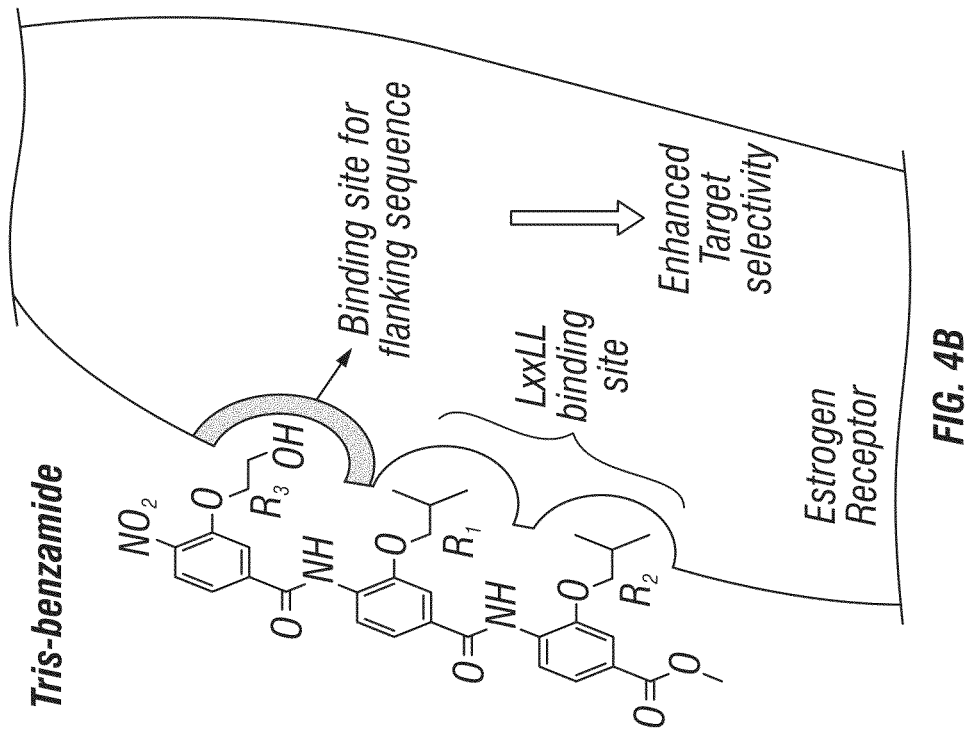
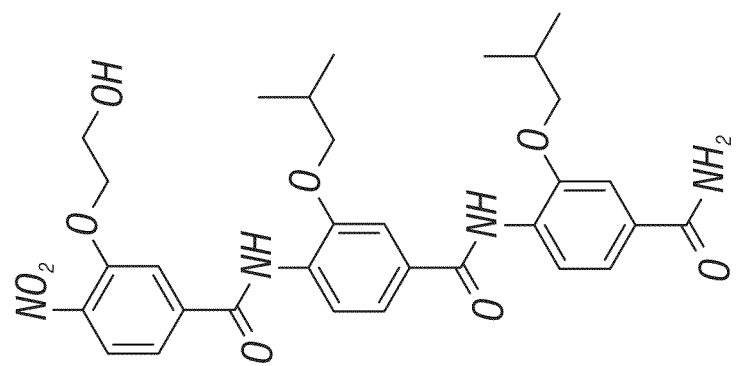
FIG. 4B
FIG. 4A

OLIGO-BENZAMIDE COMPOUNDS FOR USE IN TREATING CANCERS

PRIORITY CLAIM

This application claims benefit of priority to U.S. Provisional Application Ser. Nos. 61/563,437, filed Nov. 23, 2011, and 61/664,394, filed Jun. 26, 2012, the entire contents of both applications being hereby incorporated by reference.

FIELD OF THE INVENTION

The present invention relates in general to the field of peptidomimetics and specifically to methods of using oligo-benzamide peptidomimetic compounds in the treatment of brain, breast and ovarian cancers.

BACKGROUND OF THE INVENTION

Nuclear receptor (NR) signaling is essential for hormonal cancer development, growth, and progression at all stages of disease. NR signaling occurs via both genomic and non-genomic pathways and is mediated by NR interaction with cofactors including a scaffolding protein PELP-1. Recently, the inventors have discovered that PELP-1 interacts with several nuclear recptors (NRs) including Androgen receptor (AR) Estrogen receptor ER and that this interaction is critical for both hormonal mediated genomic and non-genomic signaling. Thus, the authors of this patent hypothesize that disruption of the interaction of nuclear receptors such as AR or ER with PELP-1 may influence hormonal mediated NR-signaling.

Peptidomimetics (also known as peptide mimetics) are small organic molecules that do not possess the peptide backbone structure, however still retain a capability to interact with the same target protein by arranging essential functional groups (i.e., pharmacophores) in a required three-dimensional pattern complimentary to a binding pocket in the protein. Since peptides and proteins adopt and utilize secondary structures (e.g., α-helix, β-sheet, and reverse turns) to make their global shapes and to recognize their binding partners, rational design of secondary structure mimetics is an important strategy in developing small molecule modulators for protein complex formation, compared to conventional high-throughput screening of a chemical library.

At present, no compounds are known that specifically inhibit the interaction with PELP-1 and NR. The identification of such compounds, and assessment of their use as anti-cancer agents, would therefore be highly desireable.

SUMMARY OF THE INVENTION

The present inventors recognized a need for improved methods of treating cancer. Stable small molecules possessing the capability to modulate NR signaling without the limitations of the peptide structure are provided that include α-helix mimetic properties that represent helical segments in the target molecules.

The oligo-benzamide peptidomimetic compound includes at least three optionally substituted benzamides, with each of the substituted benzamides having one substituent on a benzene ring. The oligo-benzamide peptidomimetic compound modulates protein-protein, protein-peptide, or protein-drug interaction to exert a variety of physiological consequences.

The present invention provides, in one aspect, a compound of formula (I or II):

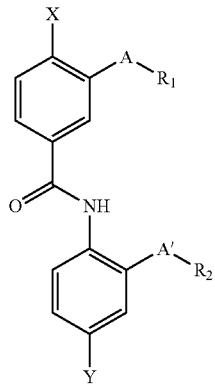

(I)

or

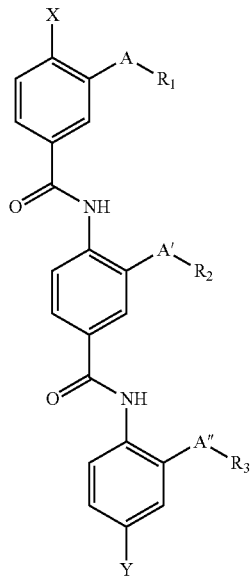

(II)

wherein:
$R_1$, $R_2$ and $R_3$ are each independently H, $C_1$-$C_{10}$ alkyl, $C_1$-$C_{10}$ alkenyl, $C_1$-$C_{10}$ alkynyl, —$(CH_2)_n$—COOR, —$(CH_2)_n$—CONRR', —$(CH_2)_n$—NRR', —$(CH_2)_n$—NH(C=NH)NRR', —$(CH_2)_n$—NRCOR', —$(CH_2)_n$—NRCOOR', —$(CH_2)_n$—OR, —$(CH_2)_n$—SR, —$(CH_2)_n$—SO$_m$R, —$(CH_2)_n$—PO$_m$R, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl group;

X is a H, —NO$_2$, —NRR', —NRCOR', —NRCOOR', —NRCONR', —OR, —SR, —COR, —COOR, —CONRCOR' wherein R and R' are independently H, —CH$_2$—Z', $C_1$-$C_{10}$ alkyl, $C_1$-$C_{10}$ alkenyl, $C_1$-$C_{10}$ alkynyl, or $C_1$-$C_{15}$ arylalkyl, each of which is optionally substituted with —COOR'', —CONR''R''', —NR''R''', —NH(C=NH)NR''R''', —NR''COR''', —NR''COOR'', —OR'', —SR'', —SO$_n$R'', or —PO$_n$R'', wherein n may be any number between 0 and 6 and R'' and R''' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl group, and wherein Z' is:

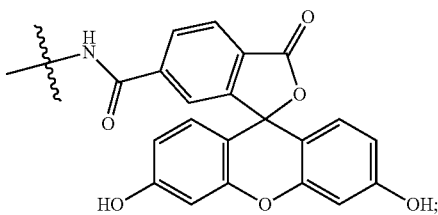 [SMILES: *NC(=O)c1ccc2c(c1)C1(OC2=O)c2ccc(O)cc2Oc2cc(O)ccc21]

and

Y is —(CH$_2$)$_n$COOR$_4$, —(CH$_2$)$_n$CONR$_4$R$_5$, —(CH$_2$)$_n$NR$_4$R$_5$, —(CH$_2$)$_n$—NR$_4$R$_5$, —(CH$_2$)$_n$—NH(C=NH)NR$_4$R$_5$, —(CH$_2$)$_n$—NR$_4$COR$_5$, —(CH$_2$)$_n$—NR$_4$COOR$_5$, —(CH$_2$)$_n$—NR$_4$CONR$_5$, —(CH$_2$)$_n$—OR$_4$, —(CH$_2$)$_n$—SR$_4$, —(CH$_2$)$_n$—SO$_m$R$_4$, —(CH$_2$)$_n$—PO$_m$R$_4$, wherein n and m may be any number between 0 and 6, R$_4$ and R$_5$ are independently selected from —H, $C_1$-$C_{10}$ alkyl, $C_1$-$C_{10}$ alkenyl, $C_1$-$C_{10}$ alkynyl, or $C_1$-$C_{15}$ optionally substituted arylalkyl group; and A, A' and A'' are independently —O—, —S—, —NR—, —(CH$_2$)n-, —CO— wherein n may be any number between 1-6.

Where X is —NO$_2$, A, A' and A'' may each be O, or R$_1$, R$_2$ and R$_3$ may independently be $C_{1-10}$ alkyl, $C_{1-10}$ hydroxyalkyl, or $C_{1-10}$ alkenyl, or A, A' and A'' may each be O and R$_1$, R$_2$ and R$_3$ and may independently be $C_{1-10}$ alkyl, $C_{1-10}$ hydroxyalkyl, or $C_{1-10}$ alkenyl. Also where X is —NO$_2$, A, A' and A'' may each be O, or R$_1$, R$_2$ and R$_3$ may independently be $C_{1-10}$ alkyl or $C_{1-10}$ hydroxyalkyl, or A, A' and A'' may each be O, and R$_1$, R$_2$ and R$_3$ may independently be $C_{1-10}$ alkyl or $C_{1-10}$ hydroxyalkyl.

Where Y is COOCH$_3$, A, A' and A'' may each be NH or R$_1$, R$_2$ and R$_3$ may independently be $C_{1-10}$ alkyl, $C_{1-10}$ hydroxyalkyl, or $C_{1-10}$ alkenyl, or A, A' and A'' may each be NH and R$_1$, R$_2$ and R$_3$ may independently be $C_{1-10}$ alkyl, $C_{1-10}$ hydroxyalkyl, or $C_{1-10}$ alkenyl. Also where Y is COOCH$_3$, A, A' and A'' may each be NH, or R$_1$, R$_2$ and R$_3$ may independently be $C_{1-10}$ alkyl or $C_{1-10}$ hydroxyalkyl, or A, A' and A'' may each be NH, and R$_1$, R$_2$ and R$_3$ may independently be $C_{1-10}$ alkyl or $C_{1-10}$ hydroxyalkyl.

Where X is —NO$_2$ and Y is —C(O)NH$_2$, A, A' and A'' may each be O, or R$_1$, R$_2$ and R$_3$ may independently be $C_{1-10}$ alkyl, $C_{1-10}$ hydroxyalkyl, or $C_{1-10}$ alkenyl, or A, A' and A'' may each be O, and R$_1$, R$_2$ and R$_3$ may independently be $C_{1-10}$ alkyl, $C_{1-10}$ hydroxyalkyl, or $C_{1-10}$ alkenyl. Also where X is —NO$_2$ and Y is —C(O)NH$_2$, A, A' and A'' may each be O, or R$_1$, R$_2$ and R$_3$ may independently be $C_{1-10}$ alkyl or $C_{1-10}$ hydroxyalkyl, or A, A' and A'' may each be O, and R$_1$, R$_2$ and R$_3$ may independently be $C_{1-10}$ alkyl or $C_{1-10}$ hydroxyalkyl.

In particular, the compound may have a formula selected from:

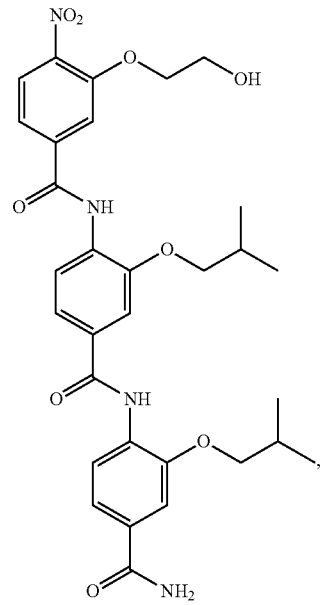

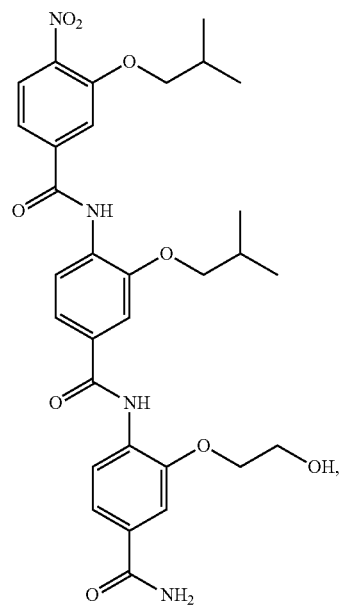

-continued
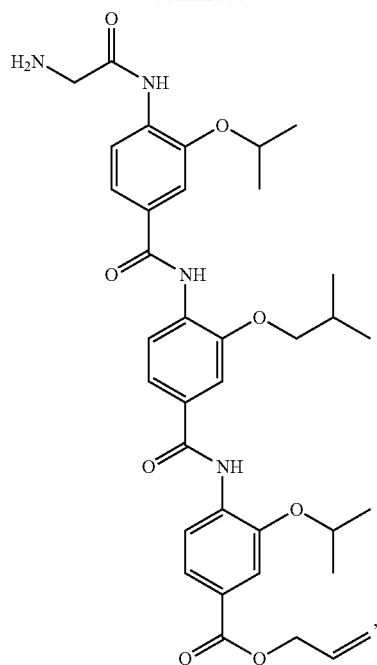
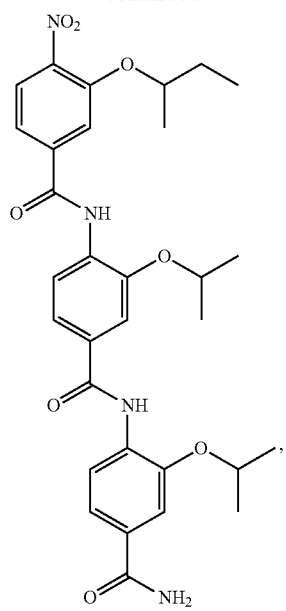
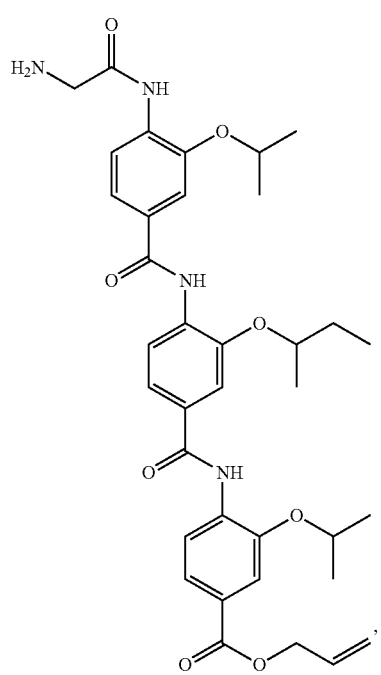
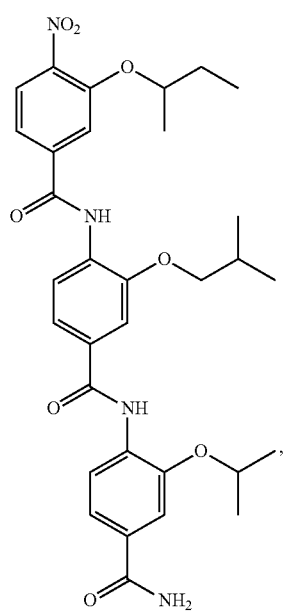

7
-continued
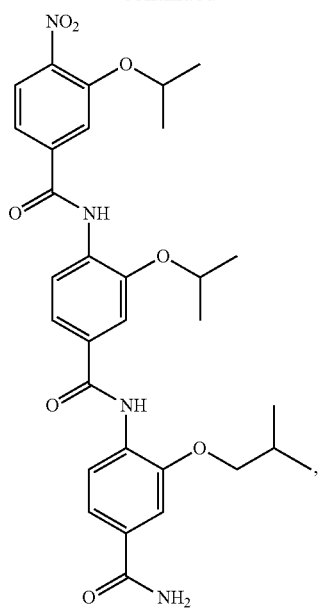
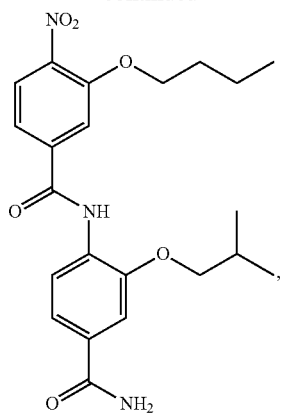
8
-continued
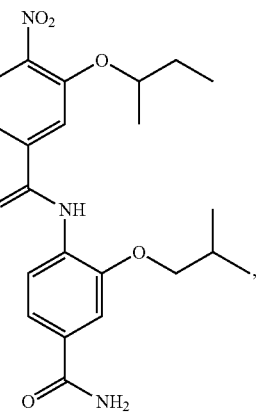
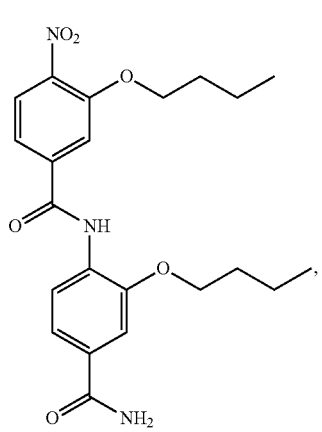
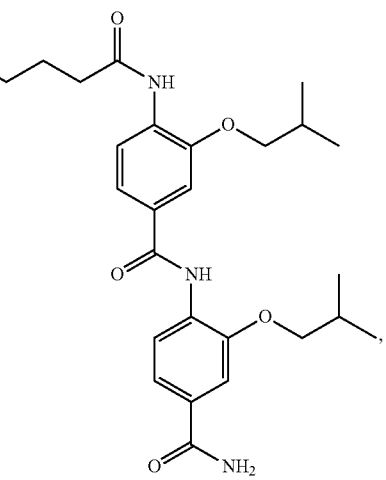

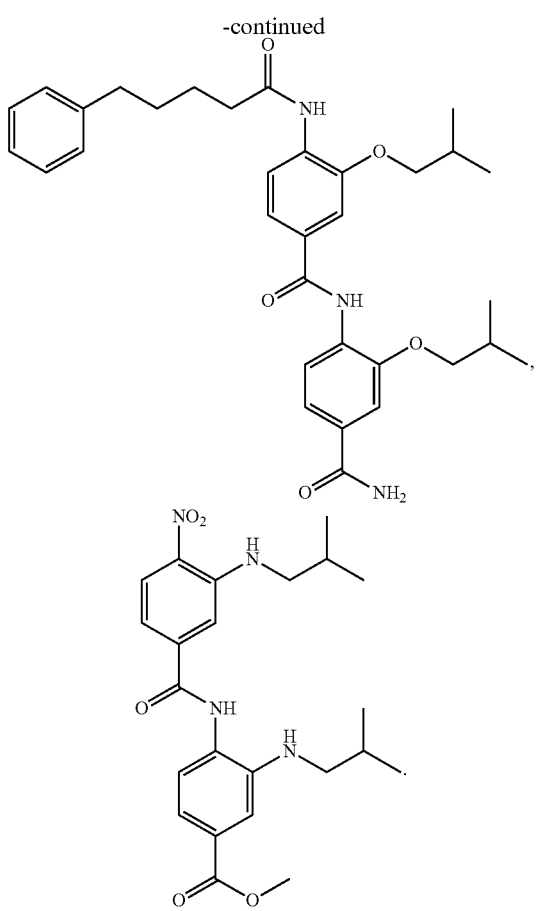

The compounds are useful in the treatment of breast, brain or ovarian tumor cell in a subject comprising administering to said subject a therapeutically sufficient amount of an oligo-benzamide peptidomimetic compound as shown above. The tumor cell may be an androgen receptor (AR)- or estrogen receptor (ER)-positive tumor cell. The tumor cell may be a carcinoma cell, such as a breast carcinoma cell. The breast cancer cell may be a triple-negative breast cancer cell. The tumor cell may be a brain cancer cell, such as a glioma. The tumor cell may be an ovarian cancer cell. Administering may comprise local, regional, systemic, or continual administration. The peptidomimetic compound may be is fused to a cell delivery domain. Inhibiting may comprise inducing growth arrest of said tumor cell, apoptosis of said tumor cell and/or necrosis of a tumor tissue comprising said tumor cell. The method may further comprise providing to said subject a second anti-cancer therapy, such as surgery, chemotherapy, radiotherapy, hormonal therapy, toxin therapy, immunotherapy, and cryotherapy. The second anti-cancer therapy may provided prior to administering said compound, after administering said compound, or at the same time as said compound. The subject may be a human. The compound may be administered at about 0.1 to about 100 mg/kg, or at about 1 to about 50 mg/kg. The compound may be administered daily, such as daily for 7 days, 2 weeks, 3 weeks, 4 weeks, one month, 6 weeks, 8 weeks, two months, 12 weeks, or 3 months. The compound may be is administered weekly, such as weekly for 2 weeks, 3 weeks, 4 weeks, 6 weeks, 8 weeks, 10 weeks, or 12 weeks. The method may further comprising assessing AR- or ER-driven gene expression in said tumor cell of said subject prior to administering said compound, or further comprising assessing AR- or ER-driven gene expression in said tumor cell of said subject after administering said compound.

The use of the word "a" or "an" when used in conjunction with the term "comprising" in the claims and/or the specification may mean "one," but it is also consistent with the meaning of "one or more," "at least one," and "one or more than one."

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. The skilled artisan will understand that typically there is no limit on the number of items or terms in any combination, unless otherwise apparent from the context.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements. It is contemplated that any method or composition described herein can be implemented with respect to any other method or composition described herein.

BRIEF DESCRIPTION OF THE DRAWINGS

For a more complete understanding of the features and advantages of the present invention, reference is now made to the detailed description of the invention along with the accompanying figures and in which:

FIGS. 4A-B. Structure of compound TK11. In TK11, to enhance the efficacy and selectivity of LXXLL peptidomimetic, an additional functional group (R₃) we introduced to the bis-benzamide core structure for emulating a side chain group found in the LXXLL sequences in PELP 1 (FIG. 4A). Schematic cartoon of TK11 binding to ER is shown (FIG. 4B).

(FIG. 5A) Results for cell line IOMM-LEE. (FIG. 5B) Results for cell line CH157

(FIG. 7A) ZR75 cells were stimulated with E2 (10-8M) for 7 days in the presence of indicated concentrations of TK11 and proliferation was measured by MTT assay. (FIG. 7B) MCF7-conshRNA and MCF7-PELP1shRNA cells were stimulated with E2 (10-8M) for three days in the presence of indicated con of TK11 and proliferation was measured by MTT assay. Insert shows expression PELP1 in the model cells. *. P<0.05; . P<0.01; *. P<0.001.

(FIG. 11A) purified ER was incubated with biotin-con or biotin-TK11 peptidomimetic in the presence of estrogen (E2). TK11 interaction with ERa was determined using avidin immunoprecipitation (IP). (FIG. 11B) MCF-7 cells were stimulated with estrogen (E2), nuclear lysates were prepared and incubated with biotin-con or biotin-TK11 peptidomimetic. TK11 interactions with endogenous ER was analyzed by avidin IP. (FIG. 11C) Purified ER, GST-PELP1 was incubated in the presence of E2 and ability of control or TK11 (500 nM) to compete PELP1 interaction with ER was determined GST pull down assay. (FIG. 11D)) Purified PELP1 was incubated with biotin-TK11 or biotin-con peptidomimetic. TK11 interaction with PELP1 was determined using avidin IP.

DETAILED DESCRIPTION OF THE INVENTION

Figure 1:
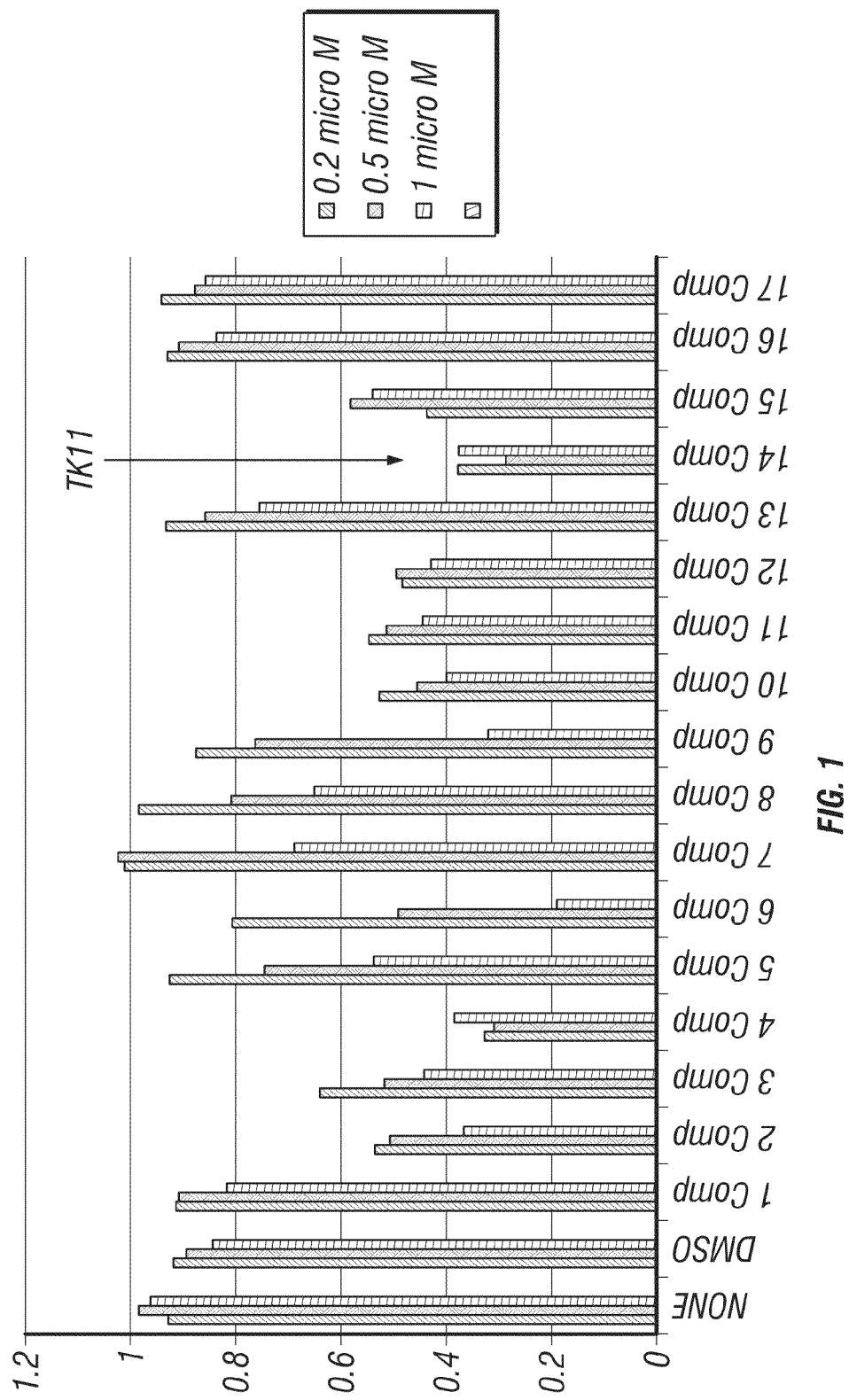
FIG. 1. Testing of oligo-benzamides for growth inhibition of triple negative breast cell line. Triple negative (ER, PR, HER2 negative breast cancer model cell line MDA-MB-231) were cultured for three days in the presence or absence of indicated concentration of oligo-benzamides and proliferation was measured by MTT assay.

Tri-benzamide contains three alkyl groups ($R_{1-3}$) that correspond to the i, and i+4 and i+7 positions of a helix. The peptidomimetics of the present invention are non-toxic under in vitro and in vivo conditions. The development of these peptidomimetics represents a quantum leap in the development of a drug to target ER signaling. Interestingly, these synthetic molecules prevent estrogen-induced translocation of ER to the nucleus and represent peptidomimetic agents that block ER nuclear translocation. In addition to improvements in the helical face and presentation of the leucines, the inventors have proven efficacy of this system against prostate cancer cell proliferation both in vitro and in vivo. Thus, in contrast to existing technology, the inventors have developed and tested active peptidomimetics against breast, brain and ovarian cancers.

These findings are exciting and represent a potentially viable method to target ER signaling pathways in various cancers. These peptidomimetics have advantages of both peptides (e.g., high efficacy and selectivity, low side effects) and small organic molecules (e.g., high enzyme stability, oral bioavailability, effective cell permeability). In addition, the novel platform using the peptidomimetics with a rigid oligo-benzamide backbone allows the presentation of selected amino acid side chains in the proper helical structure that is critical for optimal AR interactions.

I. DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "alkyl" denotes branched or unbranched hydrocarbon chains, having between about 1-20 carbons, with "lower alkyl" denoting branched or unbranched hydrocarbon chains, having between about 1-10 carbons. Non-limiting examples include methyl, ethyl, propyl, n-propyl, isopropyl, butyl, n-butyl, sec-butyl, isobutyl, t-butyl, 1-methylpropyl, pentyl, isopentyl, sec-pentyl, 2-methylpentyl, hexyl, heptyl, octyl, nonyl, decyl, octadecyl and so on. Alkyl includes cycloalkyl, such as cyclopropyl, cyclobutyl, cyclopentyl, and cyclohexyl. If not otherwise specified, these groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino, and the like to form alkyl groups such as trifluoro methyl, 3-hydroxyhexyl, 2-carboxypropyl, 2-fluoroethyl, carboxymethyl, cyanobutyl and the like.

As used herein, the term "aryl" denotes a chain of carbon atoms which form at least one aromatic ring having between about 4-20 carbon atoms, such as phenyl, naphthyl, biphenyl, anthracenyl, pyrenyl, tetrahydronaphthyl, and so on, any of which may be optionally substituted. Aryl also includes arylalkyl groups such as benzyl, phenethyl, and phenylpropyl. Aryl includes a ring system containing an optionally substituted 5 or 6-membered carbocyclic aromatic ring, said system may be bicyclic, polycyclic, bridge, and/or fused. The system may include rings that are aromatic, or partially or completely saturated. Examples of ring systems include phenyl, naphtyl, biphenyl, anthracenyl, pyrenyl, imidazolyl, triazolyl, tetraazolyl, oxazolyl, thiophenyl, pyridyl, pyrrolyl, furanyl, quinolyl, quinolinyl, indenyl, pentalenyl, 1,4-dihydronaphthyl, indanyl, benzimidazolyl, benzothiophenyl, indolyl, benzofuranyl, isoquinolinyl, and so on. If not otherwise specified, the group may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, carboxamidyl, alkoxycarbonyl, carbamyl, alkyl, alkenyl, alkynyl, nitro, amino, alkoxy, amido, imino, imido, guanidino, hydrazido, aminoxy, alkoxyamino and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, aminophenyl, amidophenyl, thiazolylphenyl, oxazolylphenyl, imidazolylphenyl, imidazolylmethylphenyl, and the like.

As used herein, the term "alkenyl" includes optionally substituted straight chain and branched hydrocarbons having between about 1-50 carbons as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbons having a mixture of double bonds and triple bonds, such as 2-penten-4-ynyl, are grouped as alkynyls herein. Alkenyl includes cycloalkenyl. Cis and trans or (E) and (Z) forms are included within the invention. If not otherwise specified, these groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino and the like to form alkyl groups such as trifluoro methyl, 3-hydroxyhexyl, 2-carboxypropyl, 2-fluoroethyl, carboxymethyl, cyanobutyl and the like.

As used herein, the term "alkynyl" includes optionally substituted straight chain and branched hydrocarbons having between about 1-50 carbons as above with at least one carbon-carbon triple bond (sp). Alkynyls include ethynyl, propynyls, butynyls, and pentynyls. Hydrocarbons having a mixture of double bonds and triple bonds, such as 2-penten-4-ynyl, are grouped as alkynyls herein. Alkynyl does not include cycloalkynyl. If not otherwise specified, these groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino and the like to form alkyl groups such as trifluoro methyl, 3-hydroxyhexyl, 2-carboxypropyl, 2-fluoroethyl, carboxymethyl, cyanobutyl and the like.

As used herein, the term "alkoxy" includes an optionally substituted straight chain or branched alkyl group having between about 1-50 carbons with a terminal oxygen linking the alkyl group to the rest of the molecule. Alkoxy includes methoxy, ethoxy, propoxy, isopropoxy, butoxy, t-butoxy, pentoxy and so on. If not otherwise specified, alkyoxy also includes any substituted alkyl group connected by an ether linkage, such as aminobutoxy, carboxyethoxy, hydroxyethoxy and so on. "Aminoalkyl", "thioalkyl", and "sulfonylalkyl" are analogous to alkoxy, replacing the terminal oxygen atom of alkoxy with, respectively, NH (or NR), S, and $SO_2$. Heteroalkyl includes alkoxy, aminoalkyl, thioalkyl, and so on.

For any of the groups above, the modifier Cn-Cn' defines both the minimum and maximum number of carbon atoms for the group. For example, "$C_2$-$C_{10}$ alkyl" designates those alkyl groups having from 2 to 10 carbon atoms (e.g., 2, 3, 4, 5, 6, 7, 8, 9, or 10, or any range derivable therein, e.g., 3 to 10 carbon atoms).

As used herein, the term "pharmaceutically acceptable" means those materials which are useful in preparing a pharmaceutical composition that is generally safe, non-toxic and neither biologically nor otherwise undesirable and includes that which is acceptable for veterinary use as well as human pharmaceutical use.

As used herein, the term "pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts, which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

II. OLIGO-BENZAMIDES AND METHODS OF SYNTHESIS

The present invention provides synthetic molecules which present the essential functionalities of corresponding peptide ligands in the proper three dimensional orientation that enables specific protein interactions, leading to either stimulation or inhibition of protein-mediated functions.

Peptidomimetics (also known as peptide mimetics) are small organic compounds which lack the peptide backbone of native peptides. Despite this modification, they still retain an ability to interact with corresponding receptors or enzymes by presenting essential chemical functionalities (i.e., pharmacophores) in characteristic three-dimensional patterns which are complimentary to the target proteins (Marshall, 1993; Ahn et al., 2002). Thereby, peptidomimetics potentially combine the advantages of peptides (e.g., high efficacy and selectivity, low side effects) and small organic molecules (e.g., high enzymatic stability and oral bioavailability).

To mimic α-helices, the present invention provides an oligo-benzamide scaffold that is rigid in structure and place and orient substituents as an α-helix does. Substitution on the rigid tris-benzamide, for instance, allowed easy placement of three functional groups ($R_{1-3}$) corresponding to the side chains of amino acids found at the i, i+4, and i+7 positions of an ideal α-helix. Furthermore, the present inventors have developed a facile synthetic route to prepare a number of tris-benzamides to represent α-helical segments of target proteins. U.S. Patent Publication 2009/0012141, incorporated herein by reference, discloses a variety of oligo-benzamide compounds and methods of synthesis therefor.

More specifically, the present invention provides an oligo-benzamide peptidomimetic compound as illustrated includes 2 or 3 optionally substituted benzamides—so called "bis" and "tris" benzamides. In addition, linkages between the optionally substituted benzamides may be varied as necessary including ester, thioester, thioamide, trans-ethylene, ethyl, methyloxy, methylamino, hydroxyethyl, carbamate, urea, imide, hydrozido, aminoxy, or other linkages known to the skilled artisan. And, the oligo-benzamide peptidomimetic compound may be attached to amino acids, oligopeptides, optionally substituted alkyl, or other structures known to the skilled artisan.

The substitution on the substituted benzamide is generally on a benzene ring and may be on the 2, 3, 4, 5, or 6 position of each of the benzene rings. The substitutions may be at the same position on each of the benzamide rings but may also be at different positions on each of the benzene rings. For example, the substitution is connected to the benzamide ring by a chemical linkage including ether, thioether, amine, amide, carbamate, urea, and carbon-carbon (single-, double-, and triple-) bonds, and the substitution comprises optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

The present invention also provides an oligo-benzamide peptidomimetic compound that includes at least two optionally substituted benzamides, with each of the substituted benzamides having one substitution on a benzene ring. The substitutions are individually attached to the benzene rings of the oligo-benzamide peptidomimetic compound by a chemical linkage including ether, thioether, amine, amide, carbamate, urea, and carbon-carbon (single-, double-, and triple-) bonds. The substitutions generally include optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

Figure 2:
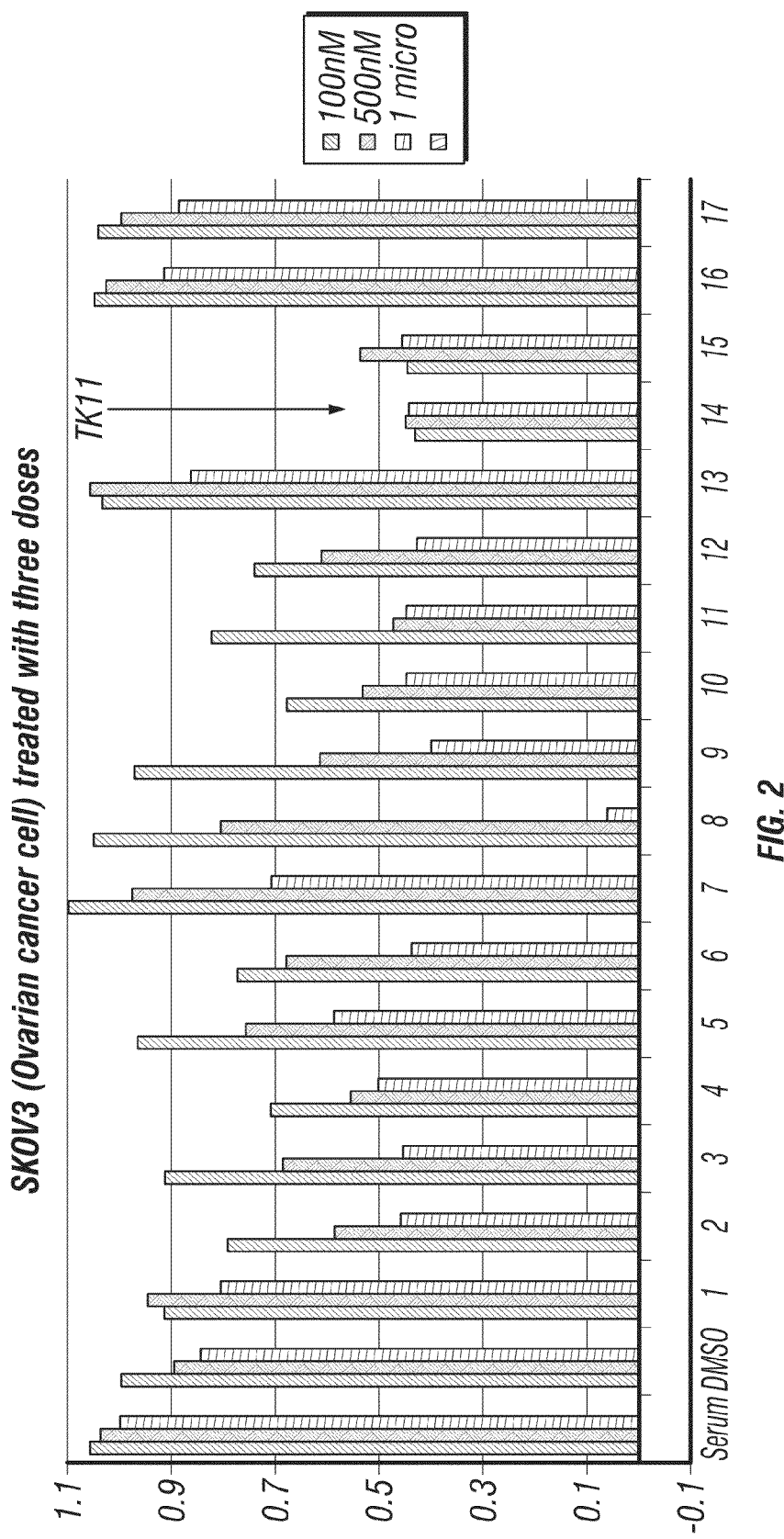
FIG. 2. Testing of oligo-benzamides for growth inhibition of ovarian cell lines. Ovarian cancer model cells (SKOV3) were cultured for three days in the presence or absence of of indicated concentrations of oligo-benzamides and the proliferation was measured by MTT assay.

U.S. Patent Publication 2009/0012141 provides synthesis schemes to prepare α-helix mimetic compounds of the present invention, for example, in FIG. 2 therein. A specific example in that document provides fifteen α-helix mimetic compounds made starting with a 4-amino-3-hydroxybenzoic acid compound 7, which was converted to an N—Ac protected methyl ester compound 8. Various alkyl groups were introduced to the hydroxyl group using a variety of alkyl halides and a base (e.g., NaOH) known to the skilled artisan. After the alkylation reaction, the methyl ester compound 9 was hydrolyzed using a base (like LiOH), and methyl 4-amino-3-hydroxybenzoate compound 10 was coupled to the free benzoic acid using a coupling reagent (like BOP), resulting in a benzamide compound 11 containing one alkyl group corresponding to the i position of a helix. These steps were repeated to synthesize oligo-benzamide compounds. Those of skill in the art would understand the broader applicability of such methods in the synthesis of other compounds such as those disclosed herein.

III. PHARMACEUTICAL FORMULATIONS AND METHODS OF TREATMENT

A. Formulations and Routes of Administration

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed (e.g., post-operative catheter). For practically any tumor, systemic delivery also is contemplated. This will prove especially important for attacking microscopic or metastatic cancer.

The active compounds may also be administered as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

The pharmaceutical peptidomimetic composition includes a therapeutically effective amount of an oligo-benzamide peptidomimetic compound or a salt, a solvent, or a derivative thereof based on an oligo-benzamide peptidomimetic compound, and one or more pharmaceutically acceptable carriers. For example, the bis- or tris-benzamide peptidomimetic composition may also include one or more additional active ingredients, diluents, excipients, active agents, lubricants, preservatives, stabilizers, wetting agents, emulsifiers, salts for influencing osmotic pressure, buffers, colorings, flavorings, aromatic substances, penetration enhancers, surfactants, fatty acids, bile salts, chelating agents, colloids and combinations thereof. The pharmaceutical peptidomimetic compound may be adapted for oral, dermatological, transdermal or parenteral administration, in the form of a solution, a emulsions, a liposome-containing formulation, a tablet, a capsule, a gel capsule, a liquid syrup, a soft gel, a suppository, an enema, a patch, an ointment, a lotion, a cream, a gel, a drop, a spray, a liquid or a powder.

B. Breast Cancer

Breast cancer refers to cancers originating from breast tissue, most commonly from the inner lining of milk ducts or the lobules that supply the ducts with milk. Cancers originating from ducts are known as ductal carcinomas; those originating from lobules are known as lobular carcinomas. There are many different types of breast cancer, with different stages (spread), aggressiveness, and genetic makeup; survival varies greatly depending on those factors. Computerized models are available to predict survival. With best treatment and dependent on staging, 10-year disease-free survival varies from 98% to 10%. Treatment includes surgery, drugs (hormonal therapy and chemotherapy), and radiation.

Worldwide, breast cancer comprises 10.4% of all cancer incidence among women, making it the second most common type of non-skin cancer (after lung cancer) and the fifth most common cause of cancer death. In 2004, breast cancer caused 519,000 deaths worldwide (7% of cancer deaths; almost 1% of all deaths). Breast cancer is about 100 times more common in women than in men, although males tend to have poorer outcomes due to delays in diagnosis.

Some breast cancers require the hormones estrogen and progesterone to grow, and have receptors for those hormones. After surgery those cancers are treated with drugs that interfere with those hormones, usually tamoxifen, and with drugs that shut off the production of estrogen in the ovaries or elsewhere; this may damage the ovaries and end fertility. After surgery, low-risk, hormone-sensitive breast cancers may be treated with hormone therapy and radiation alone. Breast cancers without hormone receptors, or which have spread to the lymph nodes in the armpits, or which express certain genetic characteristics, are higher-risk, and are treated more aggressively. One standard regimen, popular in the U.S., is cyclophosphamide plus doxorubicin (Adriamycin), known as CA; these drugs damage DNA in the cancer, but also in fast-growing normal cells where they cause serious side effects. Sometimes a taxane drug, such as docetaxel, is added, and the regime is then known as CAT; taxane attacks the microtubules in cancer cells. An equivalent treatment, popular in Europe, is cyclophosphamide, methotrexate, and fluorouracil (CMF). Monoclonal antibodies, such as trastuzumab (Herceptin), are used for cancer cells that have the HER2 mutation. Radiation is usually added to the surgical bed to control cancer cells that were missed by the surgery, which usually extends survival, although radiation exposure to the heart may cause damage and heart failure in the following years.

While screening techniques (which are further discussed below) are useful in determining the possibility of cancer, a further testing is necessary to confirm whether a lump detected on screening is cancer, as opposed to a benign alternative such as a simple cyst.

In a clinical setting, breast cancer is commonly diagnosed using a "triple test" of clinical breast examination (breast examination by a trained medical practitioner), mammography, and fine needle aspiration cytology. Both mammography and clinical breast exam, also used for screening, can indicate an approximate likelihood that a lump is cancer, and may also identify any other lesions. Fine Needle Aspiration and Cytology (FNAC), which may be done in a doctor's office using local anaesthetic if required, involves attempting to extract a small portion of fluid from the lump. Clear fluid makes the lump highly unlikely to be cancerous, but bloody fluid may be sent off for inspection under a microscope for cancerous cells. Together, these three tools can be used to diagnose breast cancer with a good degree of accuracy. Other options for biopsy include core biopsy, where a section of the breast lump is removed, and an excisional biopsy, where the entire lump is removed.

In addition vacuum-assisted breast biopsy (VAB) may help diagnose breast cancer among patients with a mammographically detected breast in women according to a systematic review. In this study, summary estimates for vacuum assisted breast biopsy in diagnosis of breast cancer were as follows sensitivity was 98.1% with 95% CI=0.972-0.987 and specificity was 100% with 95% CI=0.997-0.999. However underestimate rates of atypical ductal hyperplasia (ADH) and ductal carcinoma in situ (DCIS) were 20.9% with 95% CI=0.177-0.245 and 11.2% with 95% CI=0.098-0.128 respectively.

Breast cancer screening refers to testing otherwise-healthy women for breast cancer in an attempt to achieve an earlier diagnosis. The assumption is that early detection will improve outcomes. A number of screening test have been employed including: clinical and self breast exams, mammography, genetic screening, ultrasound, and magnetic resonance imaging.

A clinical or self breast exam involves feeling the breast for lumps or other abnormalities. Research evidence does not support the effectiveness of either type of breast exam, because by the time a lump is large enough to be found it is likely to have been growing for several years and will soon be large enough to be found without an exam. Mammographic screening for breast cancer uses x-rays to examine the breast for any uncharacteristic masses or lumps. In women at high risk, such as those with a strong family history of cancer, mammography screening is recommended at an earlier age and additional testing may include genetic screening that tests for the BRCA genes and/or magnetic resonance imaging.

Breast cancer is sometimes treated first with surgery, and then with chemotherapy, radiation, or both. Treatments are given with increasing aggressiveness according to the prognosis and risk of recurrence. Stage 1 cancers (and DCIS) have an excellent prognosis and are generally treated with lumpectomy with or without chemotherapy or radiation. Although the aggressive HER2+ cancers should also be treated with the trastuzumab (Herceptin) regime. Stage 2 and 3 cancers with a progressively poorer prognosis and greater risk of recurrence are generally treated with surgery (lumpectomy or mastectomy with or without lymph node removal), radiation (sometimes) and chemotherapy (plus trastuzumab for HER2+ cancers). Stage 4, metastatic cancer, (i.e., spread to distant sites) is not curable and is managed by various combinations of all treatments from surgery, radiation, chemotherapy and targeted therapies. These treatments increase the median survival time of stage 4 breast cancer by about 6 months.

C. Ovarian Cancer

Ovarian cancer is a cancerous growth arising from different parts of the ovary. Most (>90%) ovarian cancers are classified as "epithelial" and were believed to arise from the surface (epithelium) of the ovary. However, recent evidence suggests that the Fallopian tube could also be the source of some ovarian cancers. Since the ovaries and tubes are closely related to each other, it is hypothesized that these cells can mimic ovarian cancer. Other types arise from the egg cells (germ cell tumor) or supporting cells (sex cord/stromal).

In 2004, in the United States, 25,580 new cases were diagnosed and 16,090 women died of ovarian cancer. The risk increases with age and decreases with pregnancy. Lifetime risk is about 1.6%, but women with affected first-degree relatives have a 5% risk. Women with a mutated BRCA1 or BRCA2 gene carry a risk between 25% and 60% depending on the specific mutation. Ovarian cancer is the fifth leading cause of death from cancer in women and the leading cause of death from gynecological cancer.

Ovarian cancer causes non-specific symptoms. Early diagnosis would result in better survival, on the assumption that stage I and II cancers progress to stage III and IV cancers (but this has not been proven). Most women with ovarian cancer report one or more symptoms such as abdominal pain or discomfort, an abdominal mass, bloating, back pain, urinary urgency, constipation, tiredness and a range of other non-specific symptoms, as well as more specific symptoms such as pelvic pain, abnormal vaginal bleeding or involuntary weight loss. There can be a build-up of fluid (ascites) in the abdominal cavity.

Diagnosis of ovarian cancer starts with a physical examination (including a pelvic examination), a blood test (for CA-125 and sometimes other markers), and transvaginal ultrasound. The diagnosis must be confirmed with surgery to inspect the abdominal cavity, take biopsies (tissue samples for microscopic analysis) and look for cancer cells in the abdominal fluid. Treatment usually involves chemotherapy and surgery, and sometimes radiotherapy.

In most cases, the cause of ovarian cancer remains unknown. Older women, and in those who have a first or second degree relative with the disease, have an increased risk. Hereditary forms of ovarian cancer can be caused by mutations in specific genes (most notably BRCA1 and BRCA2, but also in genes for hereditary nonpolyposis colorectal cancer). Infertile women and those with a condition called endometriosis, those who have never been pregnant and those who use postmenopausal estrogen replacement therapy are at increased risk. Use of combined oral contraceptive pills is a protective factor. The risk is also lower in women who have had their uterine tubes blocked surgically (tubal ligation).

Ovarian cancer is classified according to the histology of the tumor, obtained in a pathology report. Histology dictates many aspects of clinical treatment, management, and prognosis. Surface epithelial-stromal tumour, also known as ovarian epithelial carcinoma, is the most common type of ovarian cancer. It includes serous tumour, endometrioid tumor and mucinous cystadenocarcinoma. Sex cord-stromal tumor, including estrogen-producing granulosa cell tumor and virilizing Sertoli-Leydig cell tumor or arrhenoblastoma, accounts for 8% of ovarian cancers. Germ cell tumor accounts for approximately 30% of ovarian tumors but only 5% of ovarian cancers, because most germ cell tumors are teratomas and most teratomas are benign (see Teratoma). Germ cell tumor tends to occur in young women and girls. The prognosis depends on the specific histology of germ cell tumor, but overall is favorable. Mixed tumors, containing elements of more than one of the above classes of tumor histology.

Ovarian cancer can also be a secondary cancer, the result of metastasis from a primary cancer elsewhere in the body. Seven percent of ovarian cancers are due to metastases while the rest are primary cancers. Common primary cancers are breast cancer and gastrointestinal cancer (a common mistake is to name all peritoneal metastases from any gastrointestinal cancer as Krukenberg cancer, but this is only the case if it originates from primary gastric cancer). Surface epithelial-stromal tumor can originate in the peritoneum (the lining of the abdominal cavity), in which case the ovarian cancer is secondary to primary peritoneal cancer, but treatment is basically the same as for primary surface epithelial-stromal tumor involving the peritoneum.

Ovarian cancer staging is by the FIGO staging system and uses information obtained after surgery, which can include a total abdominal hysterectomy, removal of (usually) both ovaries and fallopian tubes, (usually) the omentum, and pelvic (peritoneal) washings for cytopathology. The AJCC stage is the same as the FIGO stage. The AJCC staging system describes the extent of the primary Tumor (T), the absence or presence of metastasis to nearby lymph Nodes (N), and the absence or presence of distant Metastasis (M).

The AJCC/TNM staging system includes three categories for ovarian cancer, T, N and M. The T category contains three other subcategories, T1, T2 and T3, each of them being classified according to the place where the tumor has developed (in one or both ovaries, inside or outside the ovary). The T1 category of ovarian cancer describes ovarian tumors that are confined to the ovaries, and which may affect one or both of them. The sub-subcategory T1a is used to stage cancer that is found in only one ovary, which has left the capsule intact and which cannot be found in the fluid taken from the pelvis. Cancer that has not affected the capsule, is confined to the inside of the ovaries and cannot be found in the fluid taken from the pelvis but has affected both ovaries is staged as T1b. T1c category describes a type of tumor that can affect one or both ovaries, and which has grown through the capsule of an ovary or it is present in the fluid taken from the pelvis. T2 is a more advanced stage of cancer. In this case, the tumor has grown in one or both ovaries and is spread to the uterus, fallopian tubes or other pelvic tissues. Stage T2a is used to describe a cancerous tumor that has spread to the uterus or the fallopian tubes (or both) but which is not present in the fluid taken from the pelvis. Stages T2b and T2c indicate cancer that metastasized to other pelvic tissues than the uterus and fallopian tubes and which cannot be seen in the fluid taken from the pelvis, respectively tumors that spread to any of the pelvic tissues (including uterus and fallopian tubes) but which can also be found in the fluid taken from the pelvis. T3 is the stage used to describe cancer that has spread to the peritoneum. This stage provides information on the size of the metastatic tumors (tumors that are located in other areas of the body, but are caused by ovarian cancer). These tumors can be very small, visible only under the microscope (T3a), visible but not larger than 2 centimeters (T3b) and bigger than 2 centimeters (T3c).

This staging system also uses N categories to describe cancers that have or not spread to nearby lymph nodes. There are only two N categories, N0 which indicates that the cancerous tumors have not affected the lymph nodes, and N1 which indicates the involvement of lymph nodes close to the tumor. The M categories in the AJCC/TNM staging system provide information on whether the ovarian cancer has metastasized to distant organs such as liver or lungs. M0 indicates that the cancer did not spread to distant organs and M1 category is used for cancer that has spread to other organs of the body. The AJCC/TNM staging system also contains a Tx and a Nx sub-category which indicates that the extent of the tumor cannot be described because of insufficient data, respectively the involvement of the lymph nodes cannot be described because of the same reason.

Ovarian cancer, as well as any other type of cancer, is also graded, apart from staged. The histologic grade of a tumor measures how abnormal or malignant its cells look under the microscope. There are four grades indicating the likelihood of the cancer to spread and the higher the grade, the more likely for this to occur. Grade 0 is used to describe non-invasive tumors. Grade 0 cancers are also referred to as borderline tumors. Grade 1 tumors have cells that are well differentiated (look very similar to the normal tissue) and are the ones with the best prognosis. Grade 2 tumors are also called moderately well differentiated and they are made up by cells that resemble the normal tissue. Grade 3 tumors have the worst prognosis and their cells are abnormal, referred to as poorly differentiated.

The signs and symptoms of ovarian cancer are most of the times absent, but when they exist they are nonspecific. In most cases, the symptoms persist for several months until the patient is diagnosed. A prospective case-control study of 1,709 women visiting primary care clinics found that the combination of bloating, increased abdominal size, and urinary symptoms was found in 43% of those with ovarian cancer but in only 8% of those presenting to primary care clinics.

The exact cause is usually unknown. The risk of developing ovarian cancer appears to be affected by several factors. The more children a woman has, the lower her risk of ovarian cancer. Early age at first pregnancy, older age of final pregnancy and the use of low dose hormonal contraception have also been shown to have a protective effect. Ovarian cancer is reduced in women after tubal ligation.

The relationship between use of oral contraceptives and ovarian cancer was shown in a summary of results of 45 case-control and prospective studies. Cumulatively these studies show a protective effect for ovarian cancers. Women who used oral contraceptives for 10 years had about a 60% reduction in risk of ovarian cancer. (risk ratio 0.42 with statistical significant confidence intervals given the large study size, not unexpected). This means that if 250 women took oral contraceptives for 10 years, 1 ovarian cancer would be prevented. This is by far the largest epidemiological study to date on this subject (45 studies, over 20,000 women with ovarian cancer and about 80,000 controls).

The link to the use of fertility medication, such as Clomiphene citrate, has been controversial. An analysis in 1991 raised the possibility that use of drugs may increase the risk of ovarian cancer. Several cohort studies and case-control studies have been conducted since then without demonstrating conclusive evidence for such a link. It will remain a complex topic to study as the infertile population differs in parity from the "normal" population.

There is good evidence that in some women genetic factors are important. Carriers of certain mutations of the BRCA1 or the BRCA2 gene are notably at risk. The BRCA1 and BRCA2 genes account for 5%-13% of ovarian cancers and certain populations (e.g. Ashkenazi Jewish women) are at a higher risk of both breast cancer and ovarian cancer, often at an earlier age than the general population. Patients with a personal history of breast cancer or a family history of breast and/or ovarian cancer, especially if diagnosed at a young age, may have an elevated risk.

A strong family history of uterine cancer, colon cancer, or other gastrointestinal cancers may indicate the presence of a syndrome known as hereditary nonpolyposis colorectal cancer (HNPCC, also known as Lynch syndrome), which confers a higher risk for developing ovarian cancer. Patients with strong genetic risk for ovarian cancer may consider the use of prophylactic, i.e., preventative, oophorectomy after completion of childbearing. Australia being member of International Cancer Genome Consortium is leading efforts to map ovarian cancer's complete genome.

Ovarian cancer at its early stages (I/II) is difficult to diagnose until it spreads and advances to later stages (III/IV). This is because most symptoms are non-specific and thus of little use in diagnosis. When an ovarian malignancy is included in the list of diagnostic possibilities, a limited number of laboratory tests are indicated. A complete blood count (CBC) and serum electrolyte test should be obtained in all patients. The serum BHCG level should be measured in any female in whom pregnancy is a possibility. In addition, serum alpha-fetoprotein (AFP) and lactate dehydrogenase (LDH) should be measured in young girls and adolescents with suspected ovarian tumors because the younger the patient, the greater the likelihood of a malignant germ cell tumor. A blood test called CA-125 is useful in differential diagnosis and in follow up of the disease, but it by itself has not been shown to be an effective method to screen for early-stage ovarian cancer due to its unacceptable low sensitivity and specificity. However, this is the only widely-used marker currently available.

Current research is looking at ways to combine tumor markers proteomics along with other indicators of disease (i.e., radiology and/or symptoms) to improve accuracy. The challenge in such an approach is that the very low population prevalence of ovarian cancer means that even testing with very high sensitivity and specificity will still lead to a number of false positive results (i.e., performing surgical procedures in which cancer is not found intra-operatively). However, the contributions of proteomics are still in the early stages and require further refining. Current studies on proteomics mark the beginning of a paradigm shift towards individually tailored therapy.

A pelvic examination and imaging including CT scan and trans-vaginal ultrasound are essential. Physical examination may reveal increased abdominal girth and/or ascites (fluid within the abdominal cavity). Pelvic examination may reveal an ovarian or abdominal mass. The pelvic examination can include a rectovaginal component for better palpation of the ovaries. For very young patients, magnetic resonance imaging may be preferred to rectal and vaginal examination.

To definitively diagnose ovarian cancer, a surgical procedure to take a look into the abdomen is required. This can be an open procedure (laparotomy, incision through the abdominal wall) or keyhole surgery (laparoscopy). During this procedure, suspicious areas will be removed and sent for microscopic analysis. Fluid from the abdominal cavity can also be analysed for cancerous cells. If there is cancer, this procedure can also determine its spread (which is a form of tumor staging).

Women who have had children are less likely to develop ovarian cancer than women who have not, and breastfeeding may also reduce the risk of certain types of ovarian cancer. Tubal ligation and hysterectomy reduce the risk and removal of both tubes and ovaries (bilateral salpingo-oophorectomy) dramatically reduces the risk of not only ovarian cancer but breast cancer also. The use of oral contraceptives (birth control pills) for five years or more decreases the risk of ovarian cancer in later life by 50%.

Tubal ligation is believed to decrease the chance of developing ovarian cancer by up to 67% while a hysterectomy may reduce the risk of getting ovarian cancer by about one-third. Moreover, according to some studies, analgesics such as acetaminophen and aspirin seem to reduce one's risks of developing ovarian cancer. Yet, the information is not consistent and more research needs to be carried out on this matter.

Routine screening of women for ovarian cancer is not recommended by any professional society—this includes the U.S. Preventive Services Task Force, the American Cancer Society, the American College of Obstetricians and Gynecologists, and the National Comprehensive Cancer Network. This is because no trial has shown improved survival for women undergoing screening. Screening for any type of cancer must be accurate and reliable—it needs to accurately detect the disease and it must not give false positive results in people who do not have cancer. As yet there is no technique for ovarian screening that has been shown to fulfil these criteria. However in some countries such as the UK, women who are likely to have an increased risk of ovarian cancer (for example if they have a family history of the disease) can be offered individual screening through their doctors, although this will not necessarily detect the disease at an early stage.

Researchers are assessing different ways to screen for ovarian cancer. Screening tests that could potentially be used alone or in combination for routine screening include the CA-125 marker and transvaginal ultrasound. Doctors can measure the levels of the CA-125 protein in a woman's blood—high levels could be a sign of ovarian cancer, but this is not always the case. And not all women with ovarian cancer have high CA-125 levels. Transvaginal ultrasound involves using an ultrasound probe to scan the ovaries from inside the vagina, giving a clearer image than scanning the abdomen. The UK Collaborative Trial of Ovarian Cancer Screening is testing a screening technique that combines CA-125 blood tests with transvaginal ultrasound.

The purpose of screening is to diagnose ovarian cancer at an early stage, when it is more likely to be treated successfully. However the development of the disease is not fully understood, and it has been argued that early-stage cancers may not always develop into late-stage disease. With any screening technique there are risks and benefits that need to be carefully considered, and health authorities need to assess these before introducing any ovarian cancer screening programs.

The goal of ovarian cancer screening is to detect the disease at stage I. Several large studies are ongoing, but none have identified an effective technique. In 2009, however, early results from the UK Collaborative Trial of Ovarian Cancer Screening (UKCTOCS) showed that a technique combining annual CA-125 tests with ultrasound imaging did help to detect the disease at an early stage. However, it is not yet clear if this approach could actually help to save lives—the full results of the trial will be published in 2015.

Surgical treatment may be sufficient for malignant tumors that are well-differentiated and confined to the ovary. Addition of chemotherapy may be required for more aggressive tumors that are confined to the ovary. For patients with advanced disease a combination of surgical reduction with a combination chemotherapy regimen is standard. Borderline tumors, even following spread outside of the ovary, are managed well with surgery, and chemotherapy is not seen as useful.

Surgery is the preferred treatment and is frequently necessary to obtain a tissue specimen for differential diagnosis via its histology. Surgery performed by a specialist in gynecologic oncology usually results in an improved result. Improved survival is attributed to more accurate staging of the disease and a higher rate of aggressive surgical excision of tumor in the abdomen by gynecologic oncologists as opposed to general gynecologists and general surgeons.

The type of surgery depends upon how widespread the cancer is when diagnosed (the cancer stage), as well as the presumed type and grade of cancer. The surgeon may remove one (unilateral oophorectomy) or both ovaries (bilateral oophorectomy), the fallopian tubes (salpingectomy), and the uterus (hysterectomy). For some very early tumors (stage 1, low grade or low-risk disease), only the involved ovary and fallopian tube will be removed (called a "unilateral salpingo-oophorectomy," USO), especially in young females who wish to preserve their fertility.

In advanced malignancy, where complete resection is not feasible, as much tumor as possible is removed (debulking surgery). In cases where this type of surgery is successful (i.e., <1 cm in diameter of tumor is left behind ["optimal debulking"]), the prognosis is improved compared to patients where large tumor masses (>1 cm in diameter) are left behind. Minimally invasive surgical techniques may facilitate the safe removal of very large (greater than 10 cm) tumors with fewer complications of surgery.

Chemotherapy has been a general standard of care for ovarian cancer for decades, although with highly variable protocols. Chemotherapy is used after surgery to treat any residual disease, if appropriate. This depends on the histology of the tumor; some kinds of tumor (particularly teratoma) are not sensitive to chemotherapy. In some cases, there may be reason to perform chemotherapy first, followed by surgery.

For patients with stage IIIC epithelial ovarian adenocarcinomas who have undergone successful optimal debulking, a recent clinical trial demonstrated that median survival time is significantly longer for patient receiving intraperitoneal (IP) chemotherapy. Patients in this clinical trial reported less compliance with IP chemotherapy and fewer than half of the patients received all six cycles of IP chemotherapy. Despite this high "drop-out" rate, the group as a whole (including the patients that didn't complete IP chemotherapy treatment) survived longer on average than patients who received intravenous chemotherapy alone.

Some specialists believe the toxicities and other complications of IP chemotherapy will be unnecessary with improved IV chemotherapy drugs currently being developed. Although IP chemotherapy has been recommended as a standard of care for the first-line treatment of ovarian cancer, the basis for this recommendation has been challenged.

Radiation therapy is not effective for advanced stages because when vital organs are in the radiation field, a high dose cannot be safely delivered. Radiation therapy is then commonly avoided in such stages as the vital organs may not be able to withstand the problems associated with these ovarian cancer treatments.

Ovarian cancer usually has a poor prognosis. It is disproportionately deadly because it lacks any clear early detection or screening test, meaning that most cases are not diagnosed until they have reached advanced stages. More than 60% of women presenting with this cancer already have stage III or stage IV cancer, when it has already spread beyond the ovaries. Ovarian cancers shed cells into the naturally occurring fluid within the abdominal cavity. These cells can then implant on other abdominal (peritoneal) structures, included the uterus, urinary bladder, bowel and the lining of the bowel wall omentum forming new tumor growths before cancer is even suspected. The five-year survival rate for all stages of ovarian cancer is 45.5%. For cases where a diagnosis is made early in the disease, when the cancer is still confined to the primary site, the five-year survival rate is 92.7%.

D. Brain Cancer

A brain tumor is an intracranial solid neoplasm, a tumor (defined as an abnormal growth of cells) within the brain or the central spinal canal. Brain tumors include all tumors inside the cranium or in the central spinal canal. They are created by an abnormal and uncontrolled cell division, normally either in the brain itself (neurons, glial cells (astrocytes, oligodendrocytes, ependymal cells, myelin-producing Schwann cells), lymphatic tissue, blood vessels), in the cranial nerves, in the brain envelopes (meninges), skull, pituitary and pineal gland, or spread from cancers primarily located in other organs (metastatic tumors).

Any brain tumor is inherently serious and life-threatening because of its invasive and infiltrative character in the limited space of the intracranial cavity. However, brain tumors (even malignant ones) are not invariably fatal. Brain tumors or intracranial neoplasms can be cancerous (malignant) or non-cancerous (benign); however, the definitions of malignant or benign neoplasms differs from those commonly used in other types of cancerous or non-cancerous neoplasms in the body. Its threat level depends on the combination of factors like the type of tumor, its location, its size and its state of development. Because the brain is well protected by the skull, the early detection of a brain tumor only occurs when diagnostic tools are directed at the intracranial cavity. Usually detection occurs in advanced stages when the presence of the tumor has caused unexplained symptoms.

Primary (true) brain tumors are commonly located in the posterior cranial fossa in children and in the anterior two-thirds of the cerebral hemispheres in adults, although they can affect any part of the brain.

The prognosis of brain cancer varies based on the type of cancer. Medulloblastoma has a good prognosis with chemotherapy, radiotherapy, and surgical resection while glioblastoma multiforme has a median survival of only 12 months even with aggressive chemoradiotherapy and surgery. Brainstem gliomas have the poorest prognosis of any form of brain cancer, with most patients dying within one year, even with therapy that typically consists of radiation to the tumor along with corticosteroids. However, one type of brainstem glioma, a focal seems open to exceptional prognosis and long-term survival has frequently been reported.

Glioblastoma multiforme is the deadliest and most common form of malignant brain tumor. Even when aggressive multimodality therapy consisting of radiotherapy, chemotherapy, and surgical excision is used, median survival is only 12-17 months. Standard therapy for glioblastoma multiforme consists of maximal surgical resection of the tumor, followed by radiotherapy between two and four weeks after the surgical procedure to remove the cancer. This is followed by chemotherapy. Most patients with glioblastoma take a corticosteroid, typically dexamethasone, during their illness to palliate symptoms. Experimental treatments include gamma-knife radiosurgery, boron neutron capture therapy and gene transfer.

Oligodendroglioma is an incurable but slowly progressive malignant brain tumor. They can be treated with surgical resection, chemotherapy, and/or radiotherapy. For suspected low-grade oligodendrogliomas in select patients, some neuro-oncologists opt for a course of watchful waiting, with only symptomatic therapy. Tumors with the 1p/19q co-deletion have been found to be especially chemosensitive, and one source reports oligodendrogliomas to be among the most chemosensitive of human solid malignancies. A median survival of up to 16.7 years has been reported for low grade oligodendrogliomas.

Although there is no specific or singular clinical symptom or sign for any brain tumors, the presence of a combination of symptoms and the lack of corresponding clinical indications of infections or other causes can be an indicator to redirect diagnostic investigation towards the possibility of an intracranial neoplasm.

The diagnosis will often start with an interrogation of the patient to get a clear view of his medical antecedents, and his current symptoms. Clinical and laboratory investigations will serve to exclude infections as the cause of the symptoms. Examinations in this stage may include ophtamological, otolaryngological (or ENT) and/or electrophysiological exams. The use of electroencephalography (EEG) often plays a role in the diagnosis of brain tumors.

Swelling, or obstruction of the passage of cerebrospinal fluid (CSF) from the brain may cause (early) signs of increased intracranial pressure which translates clinically into headaches, vomiting, or an altered state of consciousness, and in children changes to the diameter of the skull and bulging of the fontanelles. More complex symptoms such as endocrine dysfunctions should alarm doctors not to exclude brain tumors.

A bilateral temporal visual field defect (due to compression of the optic chiasm) or dilatation of the pupil, and the occurrence of either slowly evolving or the sudden onset of focal neurologic symptoms, such as cognitive and behavioral impairment (including impaired judgment, memory loss, lack of recognition, spatial orientation disorders), personality or emotional changes, hemiparesis, hypoesthesia, aphasia, ataxia, visual field impairment, impaired sense of smell, impaired hearing, facial paralysis, double vision, or more severe symptoms such as tremors, paralysis on one side of the body hemiplegia, or (epileptic) seizures in a patient with a negative history for epilepsy, should raise the possibility of a brain tumor.

Imaging plays a central role in the diagnosis of brain tumors. Early imaging methods—invasive and sometimes dangerous—such as pneumoencephalography and cerebral angiography, have been abandoned in recent times in favor of non-invasive, high-resolution techniques, such as computed tomography (CT)-scans and especially magnetic resonance imaging (MRI). Neoplasms will often show as differently colored masses (also referred to as processes) in CT or MRI results.

Benign brain tumors often show up as hypodense (darker than brain tissue) mass lesions on cranial CT-scans. On MRI, they appear either hypo- (darker than brain tissue) or isointense (same intensity as brain tissue) on T1-weighted scans, or hyperintense (brighter than brain tissue) on T2-weighted MRI, although the appearance is variable.

Contrast agent uptake, sometimes in characteristic patterns, can be demonstrated on either CT or MRI-scans in most malignant primary and metastatic brain tumors. Perifocal edema, or pressure-areas, or where the brain tissue has been compressed by an invasive process also appears hyperintense on T2-weighted MRI might indicate the presence a diffuse neoplasm (unclear outline). This is because these tumors disrupt the normal functioning of the blood-brain barrier and lead to an increase in its permeability. However it is not possible to diagnose high versus low grade gliomas based on enhancement pattern alone.

Glioblastoma multiforme and anaplastic astrocytoma have been associated with the genetic acute hepatic porphyrias (PCT, AIP, HCP and VP), including positive testing associated with drug refractory seizures. Unexplained complications associated with drug treatments with these tumors should alert physicians to an undiagnosed neurological porphyria.

The definitive diagnosis of brain tumor can only be confirmed by histological examination of tumor tissue samples obtained either by means of brain biopsy or open surgery. The histological examination is essential for determining the appropriate treatment and the correct prognosis. This examination, performed by a pathologist, typically has three stages: interoperative examination of fresh tissue, preliminary microscopic examination of prepared tissues, and followup examination of prepared tissues after immunohistochemical staining or genetic analysis.

When a brain tumor is diagnosed, a medical team will be formed to assess the treatment options presented by the leading surgeon to the patient and his/her family. Given the location of primary solid neoplasms of the brain in most cases a "do-nothing" option is usually not presented. Neurosurgeons take the time to observe the evolution of the neoplasm before proposing a management plan to the patient and his/her relatives. These various types of treatment are available depending on neoplasm type and location and may be combined to give the best chances of survival: surgery: complete or partial ressection of the tumor with the objective of removing as many tumor cells as possible; radiotherapy; and chemotherapy, with the aim of killing as many as possible of cancerous cells left behind after surgery and of putting remaining tumor cells into a nondividing, sleeping state for as long as possible.

Survival rates in primary brain tumors depend on the type of tumor, age, functional status of the patient, the extent of surgical tumor removal and other factors specific to each case.

The primary and most desired course of action described in medical literature is surgical removal (resection) via craniotomy. Minimally invasive techniques are being studied but are far from being common practice. The prime remediating objective of surgery is to remove as many tumor cells as possible, with complete removal being the best outcome and cytoreduction ("debulking") of the tumor otherwise. In some cases access to the tumor is impossible and impedes or prohibits surgery.

Many meningiomas, with the exception of some tumors located at the skull base, can be successfully removed surgically. Most pituitary adenomas can be removed surgically, often using a minimally invasive approach through the nasal cavity and skull base (trans-nasal, trans-sphenoidal approach). Large pituitary adenomas require a craniotomy (opening of the skull) for their removal. Radiotherapy, including stereotactic approaches, is reserved for inoperable cases.

Several current research studies aim to improve the surgical removal of brain tumors by labeling tumor cells with a chemical (5-aminolevulinic acid) that causes them to fluoresce. Post-operative radiotherapy and chemotherapy are integral parts of the therapeutic standard for malignant tumors. Radiotherapy may also be administered in cases of "low-grade" gliomas, when a significant tumor burden reduction could not be achieved surgically.

Any person undergoing brain surgery may suffer from epileptic seizures. Seizures can vary from absences to severe tonic-clonic attacks. Medication is prescribed and administered to minimize or eliminate the occurrence of seizures.

Multiple metastatic tumors are generally treated with radiotherapy and chemotherapy rather than surgery. The prognosis in such cases is determined by the primary tumor, but is generally poor.

The goal of radiation therapy is to selectively kill tumor cells while leaving normal brain tissue unharmed. In standard external beam radiation therapy, multiple treatments of standard-dose "fractions" of radiation are applied to the brain. This process is repeated for a total of 10 to 30 treatments, depending on the type of tumor. This additional treatment provides some patients with improved outcomes and longer survival rates.

Radiosurgery is a treatment method that uses computerized calculations to focus radiation at the site of the tumor while minimizing the radiation dose to the surrounding brain. Radiosurgery may be an adjunct to other treatments, or it may represent the primary treatment technique for some tumors.

Radiotherapy may be used following, or in some cases in place of, resection of the tumor. Forms of radiotherapy used for brain cancer include external beam radiation therapy, brachytherapy, and in more difficult cases, stereotactic radiosurgery, such as Gamma knife, Cyberknife or Novalis Tx radiosurgery.

Radiotherapy is the most common treatment for secondary brain tumors. The amount of radiotherapy depends on the size of the area of the brain affected by cancer. Conventional external beam 'whole brain radiotherapy treatment' (WBRT) or 'whole brain irradiation' may be suggested if there is a risk that other secondary tumors will develop in the future. Stereotactic radiotherapy is usually recommended in cases involving fewer than three small secondary brain tumors.

Patients undergoing chemotherapy are administered drugs designed to kill tumor cells. Although chemotherapy may improve overall survival in patients with the most malignant primary brain tumors, it does so in only about 20 percent of patients. Chemotherapy is often used in young children instead of radiation, as radiation may have negative effects on the developing brain. The decision to prescribe this treatment is based on a patient's overall health, type of tumor, and extent of the cancer. The toxicity and many side effects of the drugs, and the uncertain outcome of chemotherapy in brain tumors puts this treatment further down the line of treatment options with surgery and radiation therapy preferred.

A shunt is used not as a cure but to relieve symptoms by reducing hydrocephalus caused by blockage of cerebrospinal fluid.

Researchers are presently investigating a number of promising new treatments including gene therapy, highly focused radiation therapy, immunotherapy and novel chemotherapies. A variety of new treatments are being made available on an investigational basis at centers specializing in brain tumor therapies.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials & Methods

Synthesis of TK11. To enhance the efficacy and selectivity of LXXLL peptidomimetics, an additional functional group ($R_3$) was introduced to the bis-benzamide core structure for emulating a side chain group found in the LXXLL sequences in PELP 1. Following the established solid-phase synthetic method, TK11 and other analogues used in these studies were synthesized.

Model cells. Human Breast cancer cells MCF7, ZR75, glioma cells U87, T98G, LN229, and the ovarian cancer cell line SKOV3 were obtained from the American Type Culture Collection (ATCC) and were maintained using ATCC recommended media.

Cell proliferation assays. Cell proliferation rates were measured by using MTT Cell Viability Assay in 96-well micro plates. Model cells were seeded in 96-well plates ($2 \times 10^3$ cells/well) in DMEM or RPMI medium containing 10% serum. After an overnight incubation, cells were treated with varying concentrations of oligo-benzamides for 72 h and growth inhibition was determined by using traditional MTT assay (Sigma) following manufacturer's instructions.

Estrogen mediated proliferation assays. MCF7, ZR75 model cell lines were synchronized to G0/G1 phase by serum starvation for 3 days in 0.5% dextran charcoal-treated serum containing medium and released into cell cycle by addition of $10^{-8}$ M $E_2$ in the presence or absence of TK11 Cell proliferation rate was measured in 96-well format using CellTiter-Glo Luminescent Cell Viability Assay (Promega) following manufacturer's instructions.

Therapy resistance assays. Tamoxifen (Tam) therapy resistant MCF7-HER2 and MCF7-TAM cells were cultured in tamoxifen (10-7M) containing media in the presence or absence of TK11 and proliferation was measured by MTT assay (Sigma) following manufacturer's instructions.

Migration assays. Models cells MCF7 and MCF7-PELP1 were cultured in steroid free medium for two days, treated with E2 (10-8M) in the presence or absence of TK11 (500 nM) and cell migration potential was analyzed using a Boyden chamber assay (Promega) as per manufacturer instructions.

Reporter Gene Assays. Model cells were seeded in 6-well plates. After overnight incubation, the cells were transfected with ERE-Luc+ER plasmids using fugene for 6 h. Then, 24 h after transfection, cells were treated with vehicle or TK11 for an additional 24 h. Each transfection was carried out in triplicate and normalized with the β-gal activity and total protein concentration. Luciferase activity was measured by using the luciferase assay system (Promega, Madison, Wis.).

Binding Assays. Purified commercially available estrogen receptor (ER) was incubated with biotin-con or biotin-TK11 peptidomimetic in the presence of estrogen (E2). TK11 interaction with ER was determined using avidin immunoprecipitation (IP) followed by western blotting. For some experiments, MCF-7 cells were stimulated with estrogen (E2), nuclear lysates were prepared and incubated with biotin-con or biotin-TK11 peptidomimetic. TK11 interactions with endogenous ER were analyzed by avidin IP. For some experiments, purified ER, GST-PELP1 was incubated in the presence of E2 and ability of control or TK11 (500 nM) to compete PELP1 interaction with ER was determined GST pull down assay.

RESULTS

Ligand independent activation of the androgen receptor (AR) may involve (1) AR mutants or splicing variants that lack a ligand-binding domain (LBD) such ARv7 or (2) have gain of function mutation in AR (largely occurring in the LBD and conferring ligand promiscuity or in constitutively active conformation) or (3) undergo activation by other cofactors or receptors. AR interacts with several protein cofactors such as the scaffolding protein PELP1 (proline-, glutamic acid-, and leucine-rich), heat shock proteins (Hsp-27, Hsp-90), and others that are involved in AR nuclear translocation and activation of both genomic and non-genomic signals[1]. The network of interactions between AR and its protein cofactors is critical for AR signaling both in ligand dependent and indepenent pathways. Disruption of interactions between AR and critical cofactors by targeting structural motifs involved in protein-protein interactions (PPIs) may block both ligand dependent and indepenent activation of AR and represent a novel therapeutic approach for patients with castrate resistant prostate cancer (CRPC).

In the castrate state, CRPC cells grow in an androgen depleted environment. Recently, splice variants of the AR that lack the ligand binding domain (LBD) have been shown to be dramatically upregulated in CRPC and appear to be the primary driver of androgen-responsive genes in CRPC. AR splice variants include the commonly seen ARv7 and AR567. Since these splice variants lack the LBD, they contain the N-terminus of AR and are ligand indepenent. These splice variants are thus not affected by agents targeting the LBD of AR, including all strategies aimed at androgen deprivation and newer agents in development including MDV3100. There is a critical and unmet need for agents targeting the N-terminus of the AR.

In an elegant study, Dehm et al. (2007) molecularly dissected the TAU5 domain in the N-terminus of the AR and showed that the $^{435}$WxxLF$^{439}$ motif on AR was fully responsible for its ligand independent activity. Mechanistically, WxxLF did not rely on an interaction with the AR LBD to mediate ligand independent AR activity. Rather, WxxLF functioned as an autonomous trans activation domain. While the overall structure of the N-terminus of AR is poorly understood, the identification of this specific protein motif on AR enables potential targeting of PPIs involved in ligand independent activation of AR. Thus, small molecule inhibitors for the interaction of critical cofactors with the WxxLF motif on the AR may block ligand independent AR-mediated signaling pathways.

Figure 3:
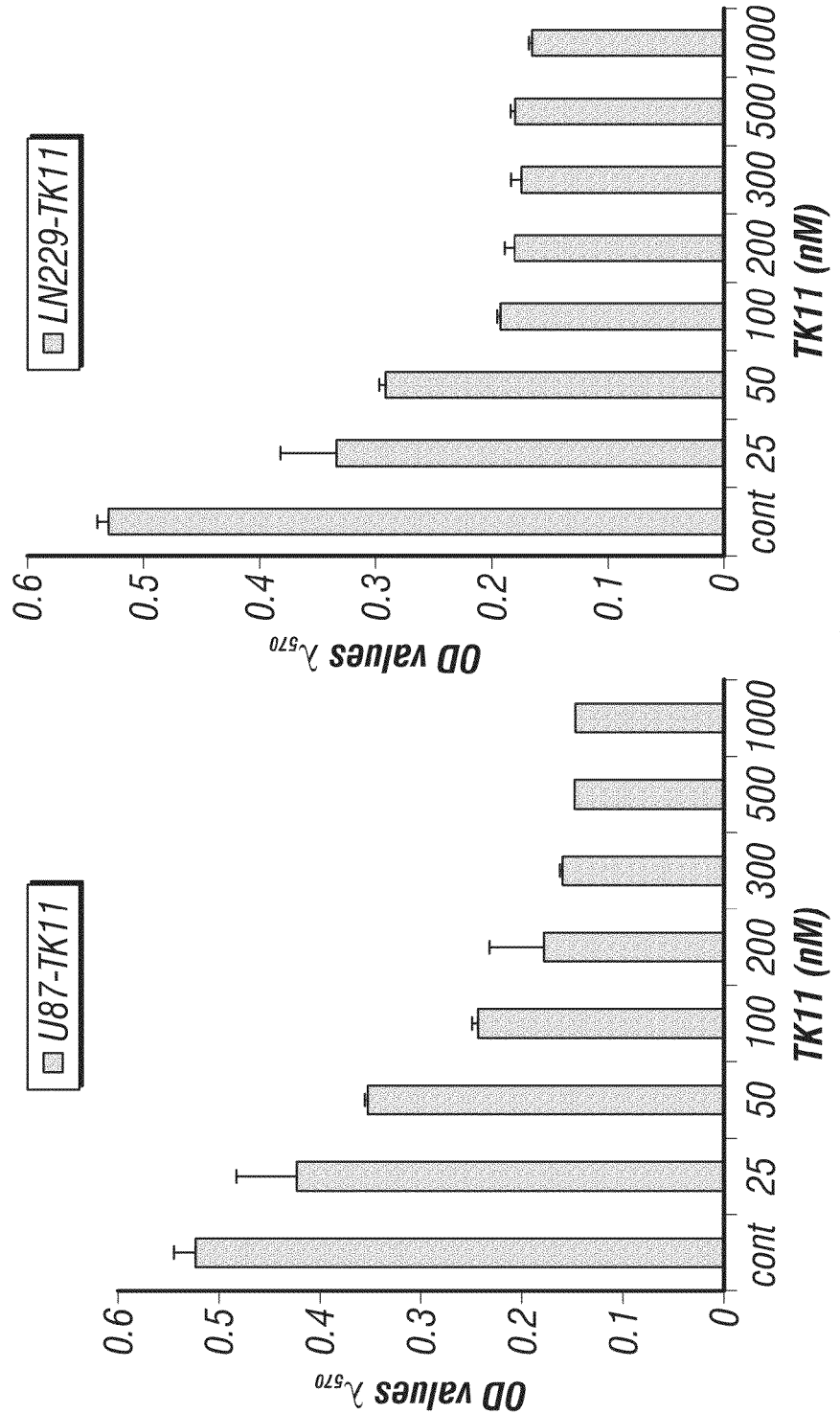
FIG. 3. Testing of oligo-benzamides for growth inhibitor of two brain cancer cell lines. Brain tumor Glioma model cells (U87 and LN229) were cultured for three days in the presence or absence of indicated concentration of TK11 and proliferation was measured by MTT assay. Results for cell line U87U are shown in the left panel. Results for cell line LN229 are shown in the right panel.
Figures 5A, 5B:
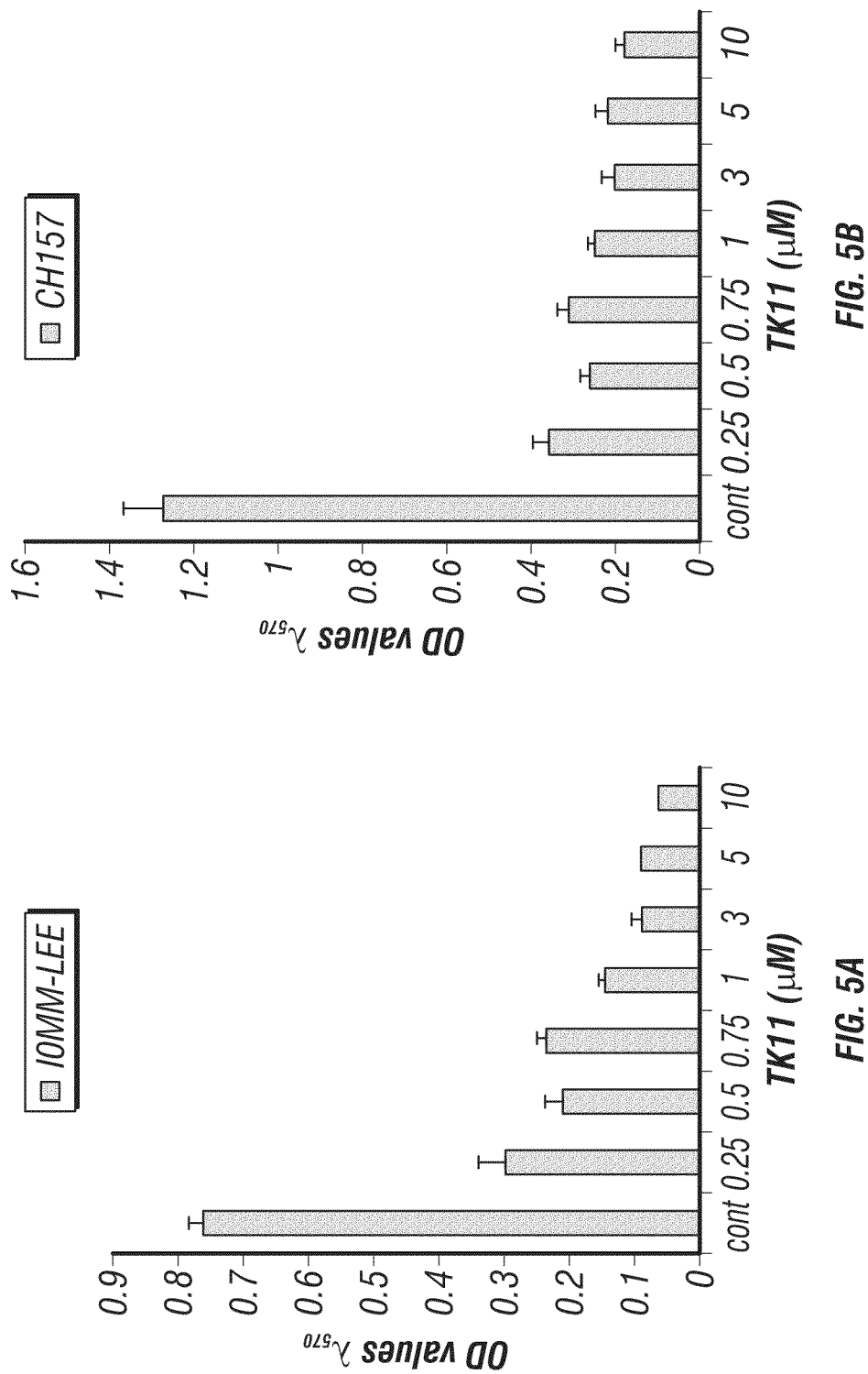
FIGS. 5A-B. Testing of oligo-benzamide (TK 11) for growth inhibitor of two meningioma brain cancer cell lines. Brain tumor Meningioma model cells (IOMM-LEE and CH157) were cultured for three days in the presence or absence of of indicated concentration of TK11 and proliferation was measured by MTT assay.
Figure 6:
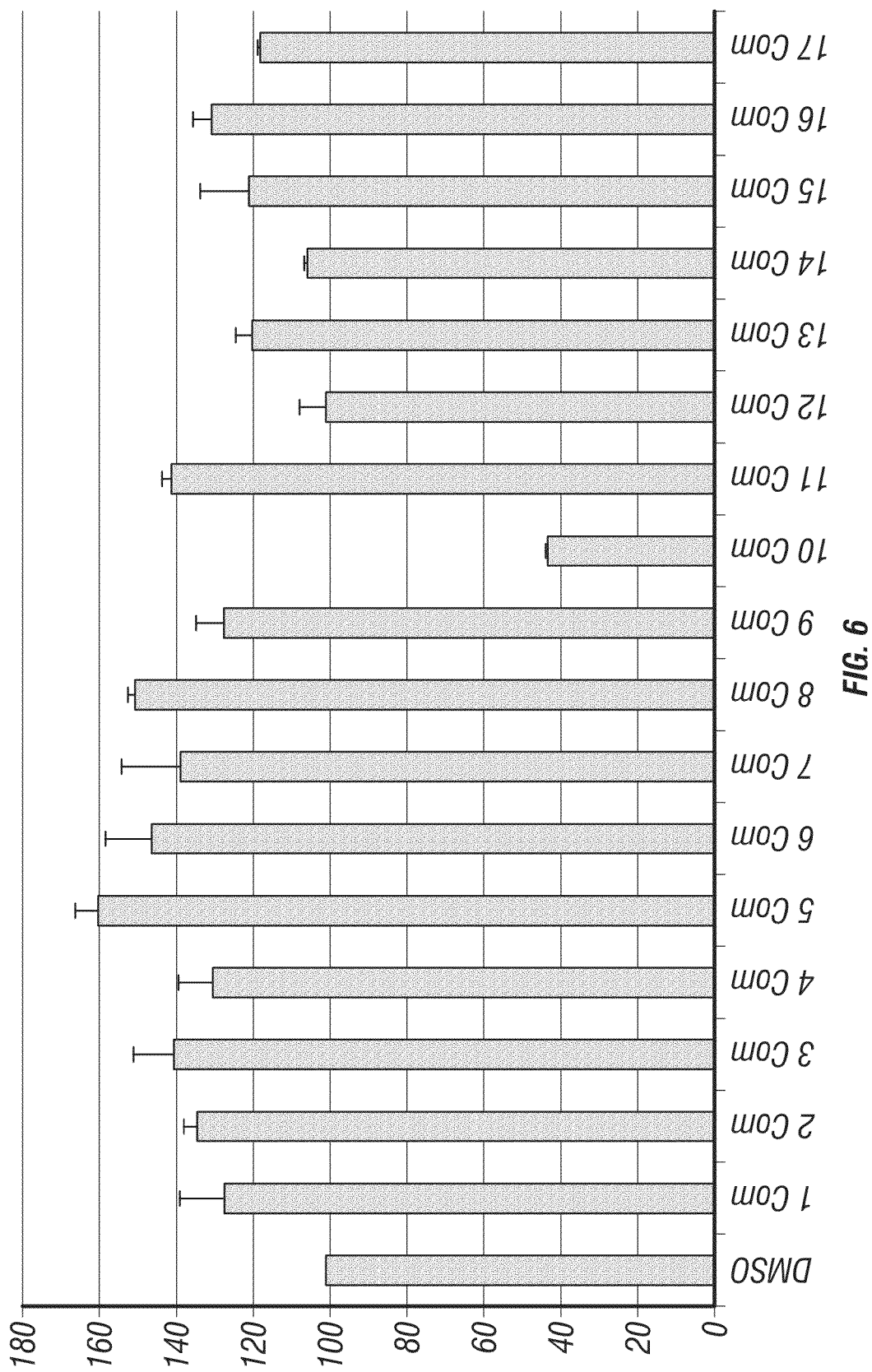
FIG. 6. Testing of oligo-benzamides on growth of normal ovarian cells. IOSE are immortalized normal ovarian cells. Interestingly, TK11 showed weak potency in inhibiting growth of normal ovarian cancer cells but higher specificity for tumor cells. This suggest that TK 11 will have less side effects.

The inventors tested a number of oligo-benzamides on breast cancer, ovarian cancer, and brain cancer cell lines. Several compounds showed high efficacy showing potent growth inhibition of these cancer cell lines. In particular, the compound called TK11 (FIG. 4) showed high potencies on triple negative breast cancer cell line (FIG. 1), which is the target of intensive research in breast cancer field. And, this compound also showed high potency in ovarian cancer cell line SKOV3 (FIG. 2) and brain cancer Glioma models (U87 and LN229) (FIGS. 3A-B). Further, TK11 also showed high potency on brain malignant tumor Meningioma model cells (IOMM-Lee and CH-157) (FIG. 5A). However, TK11 showed no activity on normal human ovarian surface epithelial cells (IOSE cells) (FIG. 6) suggesting it activity is more toward cancerous cells and also indicated less side effects.

Figure 7B:
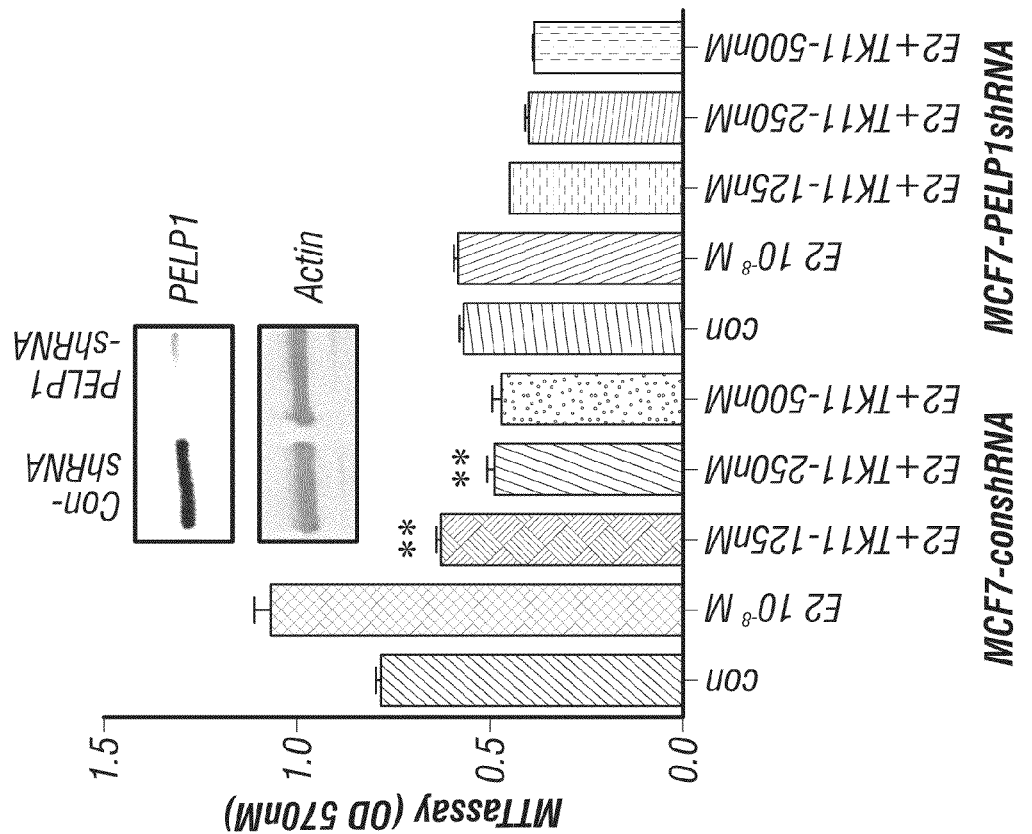
FIGS. 7A-B. Testing of oligo-benzamides for growth inhibition of estrogen driven proliferation.
Figure 7A:
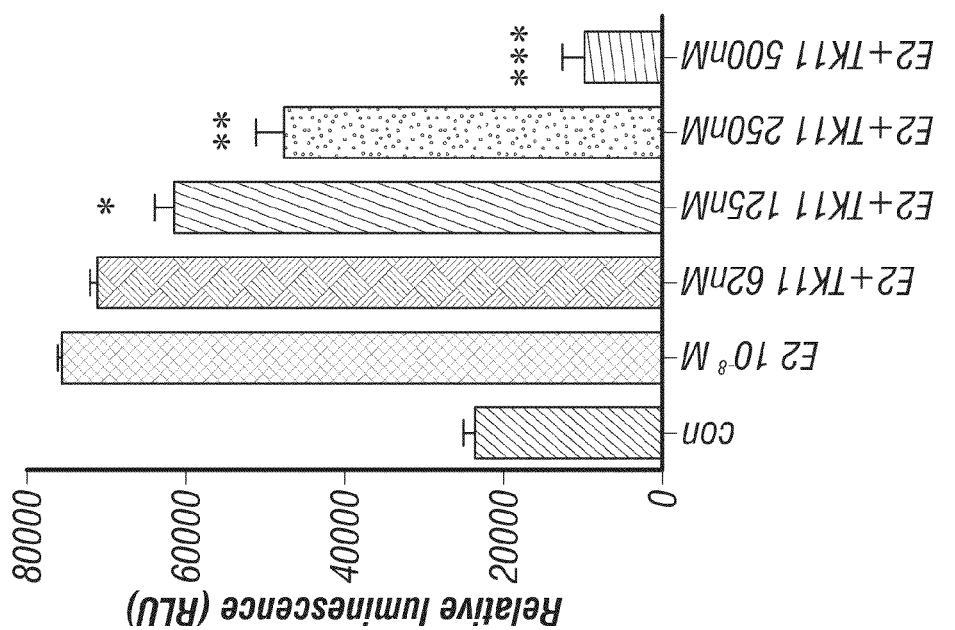
Figure 8:
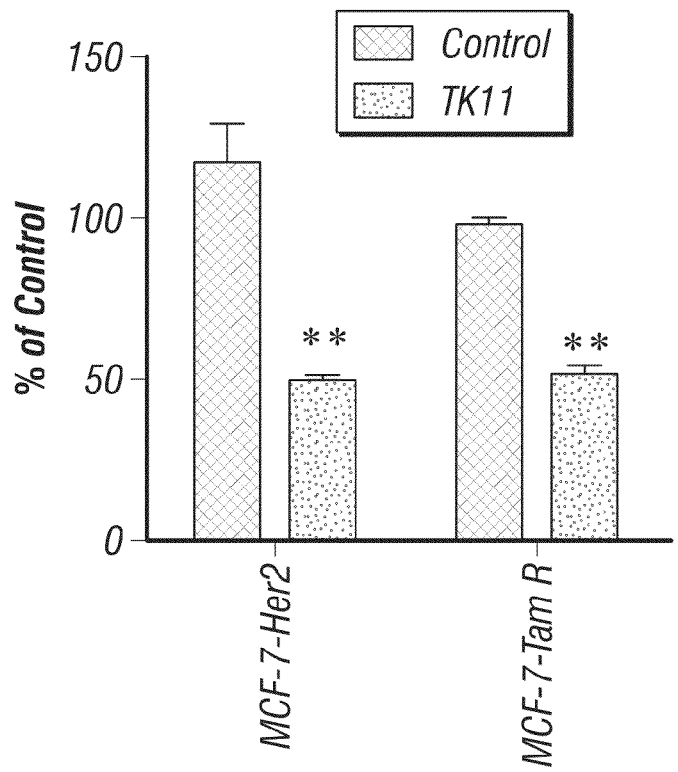
FIG. 8. Testing of oligo-benzamides for growth inhibition of hormonal therapy resistant cells. Therapy resistance is a major clinical problem. Tamoxifen (Tam) therapy resistant MCF7-HER2 and MCF7-TAM cells were cultured in tam (10-7M) containing media in the presence or absence of TK11 and proliferation was measured by MTT assay. MCF7-Her and MCF7-Tam model cells exhibit resistance to antiestrogen therapy. Interstingly, TK11 significantly inhibited the growth of the resistant cells. *, P<0.05.
Figure 9:
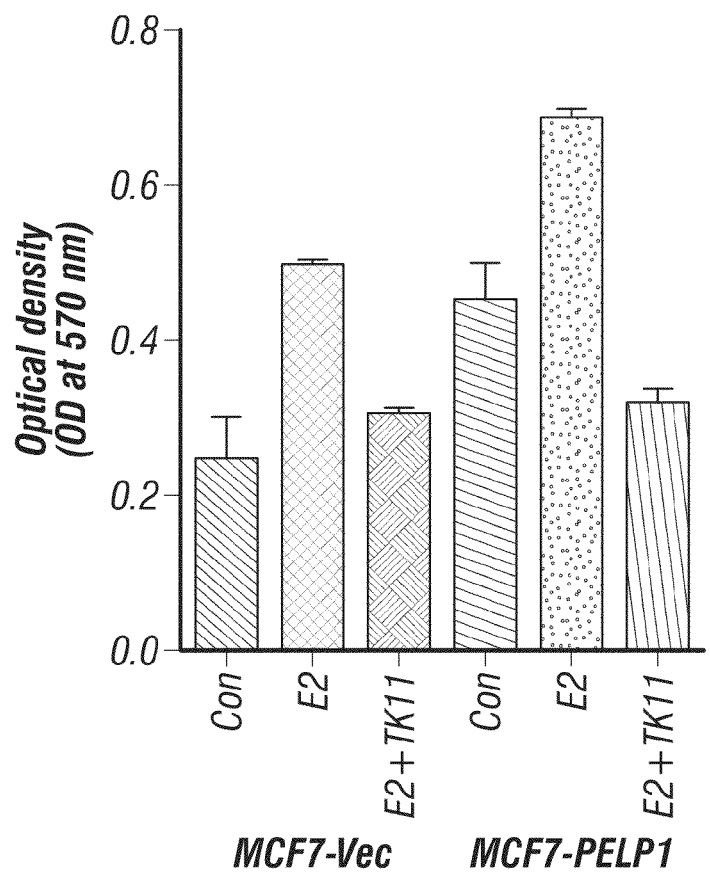
FIG. 9. TK11 affects the migration of estrogen receptor ER-positive breast cancer cells. Models cells MCF7 and MCF7-PELP1 cells cultured in steroid free mediaum were treated with E2 (10-8M) in the presence or absence of TK11 (500 nM) and cell migration potential was analyzed using a Boyden chamber assay. **, P 0.001, t-test.

In estrogen induced proliferation assays using ER-positive ZR75 model cells, TK11 inhibited growth with an $IC_{50}$=220 nM (FIG. 7A) and in assays using ER-positive MCF7 cells with $IC_{50}$=125 nM (FIG. 7B). Interestingly, PELP1 knockdown diminished proliferation upon E2 stimulation and TK11 showed minimal effects in PELP1 knockdown cells (FIG. 7B). These results further suggest that TK11 has potential to inhibit estrogen mediated proliferation and TK11 activity depends on PELP1 expression in cells. TK11 also reduced the proliferation of therapy resistant ER-positive cells using MCF7-HER2 and MCF7-Tam model cells. Both of these model cells exhibit resistance to Tamoxifen therapy. Results showed that TK11 has significant activity on both cell lines tested (FIG. 8). These results suggest that TK11 may have utility in therapeutic targeting of therapy resistance. In boyden chanber assays using MCF7 and MCF7-PELP1 cells, TK11 demonstrated potential to reduce estrogen mediated cell migration potential (FIG. 9). These results suggest TK11 will have utility in curbing metastasis.

Figure 10:
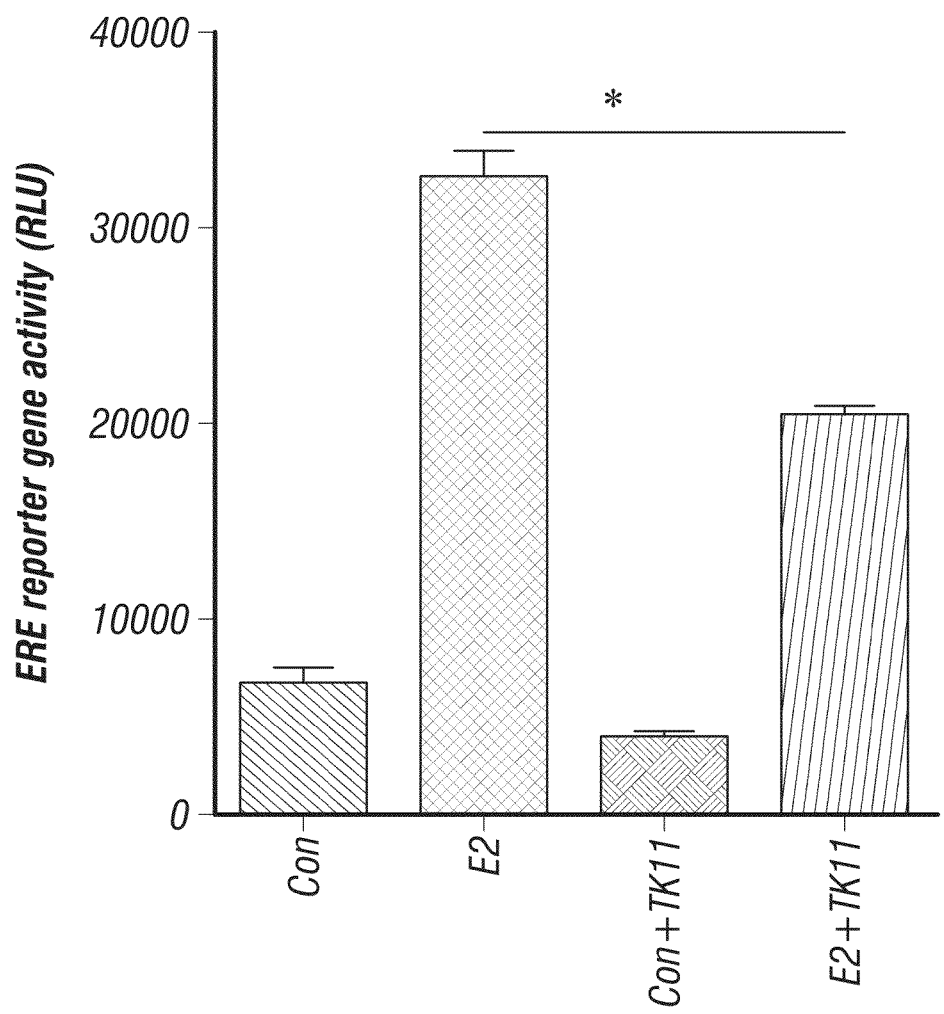
FIG. 10. TK11 affects estrogen responsive element (ERE) reporter activity. HEK 293 cells transfected with ERa and ERE-Luc vectors, after 48 h, treated with E2 (10-8M) and after 12 h, the reporter gene activity was measured. *, P<0.05.
Figure 11D:
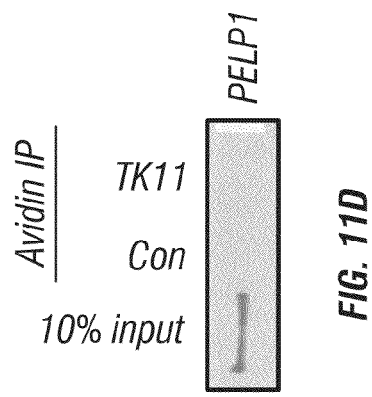
FIGS. 11A-D. TK11 interact with estrogen receptor (ER).
Figure 11C:
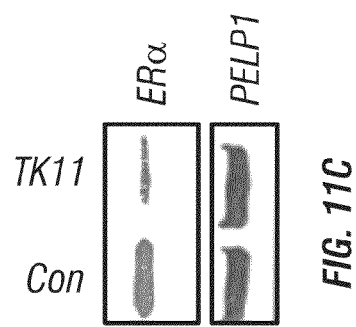
Figure 11B:
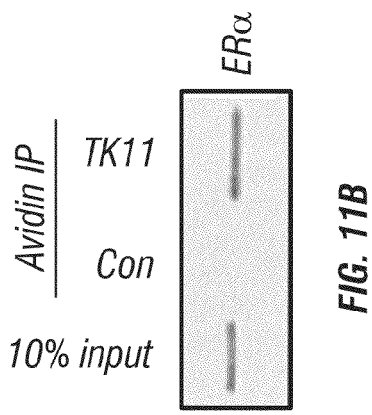
Figure 11A:
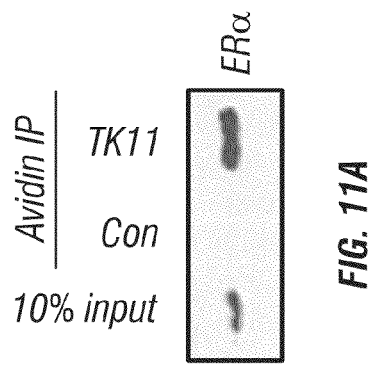

70% of the breast cancers represent ER-positive subtype and they represent major class of breast cancer and their growth is modulated by estrogen receptor. The inventors tested whether TK11 modulates ER coactivator activation functions using estrogen response element (ERE) reporter gene assays. Reporter based studies showed that TK11 has potential to interfere with estrogen mediate transactivation (FIG. 10). TK11 has potential to bind estrogen receptor ER and compete PELP1 binding to ER (FIGS. 11A-D). Biotin-TK11 pull down assays demonstrated that TK11 has ability to interact both purified ER as well as endogenous ER in MCF7 nuclear extracts (FIGS. 11A-B). In competition assays, TK11 has potential to inhibit PELP1 interaction with ER (FIG. 11C), however, TK11 failed to directly interact with PELP1 (FIG. 11D). These results suggest that TK11 direct interaction with ER prevent PELP1 interactions with ER.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Publication 2009/0012141

Dehm et al., *Cancer Res.* 67(20):10067-77, 2007

What is claimed:

1. A method of inhibiting a breast, brain or ovarian tumor cell in a subject comprising administering to said subject a therapeutically sufficient amount of an oligo-benzamide peptidomimetic compound as shown in formula (I or II):

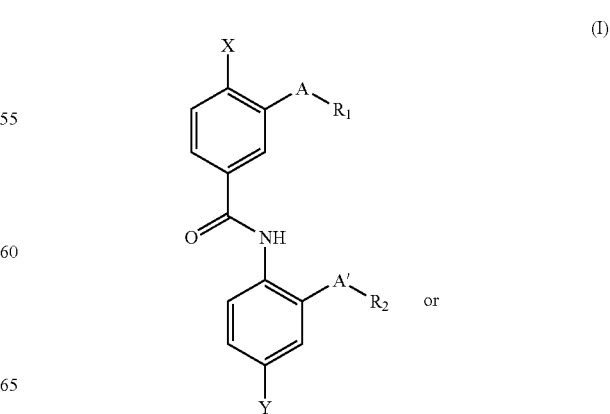

-continued (II)

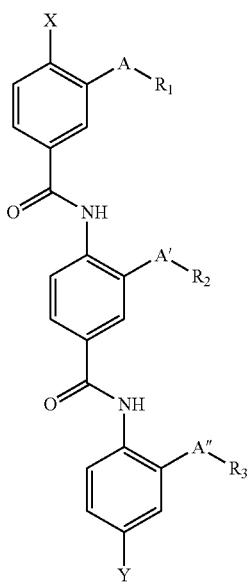

wherein:
R₁, R₂ and R₃ are each independently H, $C_1$-$C_{10}$ alkyl, $C_1$-$C_{10}$ alkenyl, $C_1$-$C_{10}$ alkynyl, —(CH₂)ₙ—COOR, —(CH₂)ₙ—CONRR', —(CH₂)ₙ—NRR', —(CH₂)ₙ—NH(C=NH)NRR', —(CH₂)ₙ—NRCOR', —(CH₂)ₙ—NRCOOR', —(CH₂)ₙ—OR, —(CH₂)ₙ—SR, —(CH₂)ₙ—SOₘR, —(CH₂)ₙ—POₘR, wherein n and m may be any number between 0 and 6 and R and R' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl group;

X is a —NO₂, —NRR', —NRCOR', —NRCOOR', —NRCONR', —OR, and —SR, wherein R and R' are independently H, —CH₂—Z', $C_1$-$C_{10}$ alkyl, $C_1$-$C_{10}$ alkenyl, $C_1$-$C_{10}$ alkynyl, or $C_1$-$C_{15}$ arylalkyl, each of which is optionally substituted with —COOR'', —CONR''R''', —NR''R''', —NH(C=NH)NR''R''', —NR''COR''', —NR''COOR''', —OR'', —SR'', —SOₙR'', or —POₙR'', wherein n may be any number between 0 and 6 and R'' and R''' may be a H, $C_1$-$C_{10}$ alkyl, $C_1$-$C_{10}$ alkenyl, $C_1$-$C_{10}$ alkynyl, or $C_1$-$C_{15}$ optionally substituted arylalkyl group, and wherein Z' is:

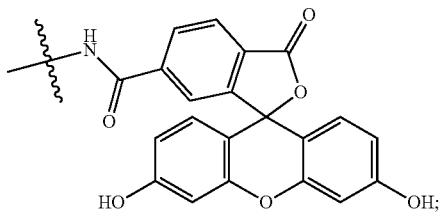 [SMILES: *NC(=O)c1ccc2c(c1)C1(OC2=O)c2ccc(O)cc2Oc2cc(O)ccc21]

and
Y is —(CH₂)ₙCOOR₄, —(CH₂)ₙCONR₄R₅, —(CH₂)ₙNR₄R₅, —(CH₂)ₙ—NR₄R₅, —(CH₂)ₙ—NH(C=NH)NR₄R₅, —(CH₂)ₙ—NR₄COR₅, —(CH₂)ₙ—NR₄COOR₅, —(CH₂)ₙ—NR₄CONR₅, —(CH₂)ₙ—OR₄, —(CH₂)ₙ—SR₄, —(CH₂)ₙ—SOₘR₄, —(CH₂)ₙ—POₘR₄, wherein n and m may be any number between 0 and 6,
R₄ and R₅ are independently selected from —H, $C_1$-$C_{10}$ alkyl, $C_1$-$C_{10}$ alkenyl, $C_1$-$C_{10}$ alkynyl, or $C_1$-$C_{15}$ optionally substituted arylalkyl group; and A, A' and A" are independently —O—, —S—, —NR—, —(CH₂)ₙ—, —CO— wherein n may be any number between 1-6.

2. The method of claim 1, wherein X is —NO₂.
3. The method of claim 1, wherein Y is —C(O)NH₂.
4. The method of claim 2, wherein A, A' and A" are each O.
5. The method of claim 2, wherein R₁, R₂ and R₃ are independently $C_{1-10}$ alkyl, $C_{1-10}$ hydroxyalkyl, or $C_{1-10}$ alkenyl.
6. The method of claim 4, wherein R₁, R₂ and R₃ are independently $C_{1-10}$ alkyl, $C_{1-10}$ hydroxyalkyl, or $C_{1-10}$ alkenyl.
7. The method of claim 2, wherein R₁, R₂ and R₃ are independently $C_{1-10}$ alkyl or $C_{1-10}$ hydroxyalkyl.
8. The method of claim 4, wherein R₁, R₂ and R₃ are independently $C_{1-10}$ alkyl or $C_{1-10}$ hydroxyalkyl.
9. The method of claim 1, wherein Y is COOCH₃.
10. The method of claim 1, wherein A, A' and A" are each NH.
11. The method of claim 9, wherein A, A' and A" are each NH.
12. The method of claim 9, wherein R₁, R₂ and R₃ are independently $C_{1-10}$ alkyl, $C_{1-10}$ hydroxyalkyl, or $C_{1-10}$ alkenyl.
13. The method of claim 11, wherein R₁, R₂ and R₃ are independently $C_{1-10}$ alkyl or $C_{1-10}$ hydroxyalkyl.
14. The method of claim 1, wherein X is —NO₂ and Y is —C(O)NH₂.
15. The method of claim 14, wherein A, A' and A" are each O.
16. The method of claim 14, wherein R₁, R₂ and R₃ are independently $C_{1-10}$ alkyl, $C_{1-10}$ hydroxyalkyl, or $C_{1-10}$ alkenyl.
17. The method of claim 15, wherein R₁, R₂ and R₃ are independently $C_{1-10}$ alkyl, $C_{1-10}$ hydroxyalkyl, or $C_{1-10}$ alkenyl.
18. The method of claim 14, wherein R₁, R₂ and R₃ are independently $C_{1-10}$ alkyl or $C_{1-10}$ hydroxyalkyl.
19. The method of claim 15, wherein R₁, R₂ and R₃ are independently $C_{1-10}$ alkyl or $C_{1-10}$ hydroxyalkyl.
20. The method of claim 1, having the formula selected from:

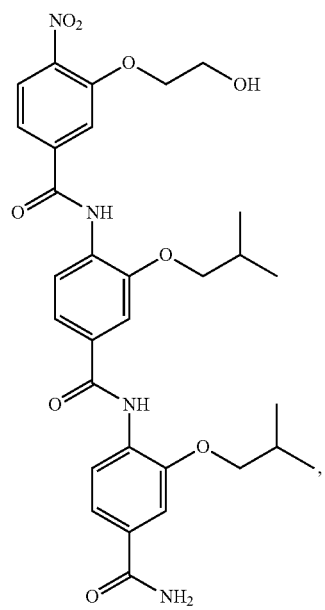

35
-continued
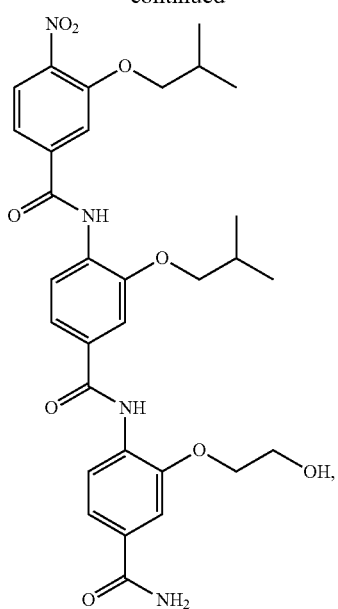
36
-continued
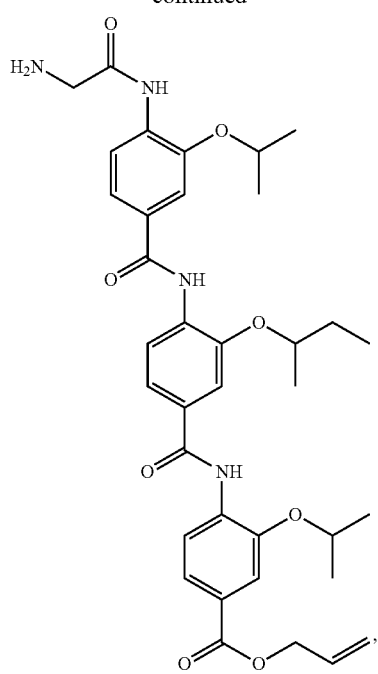
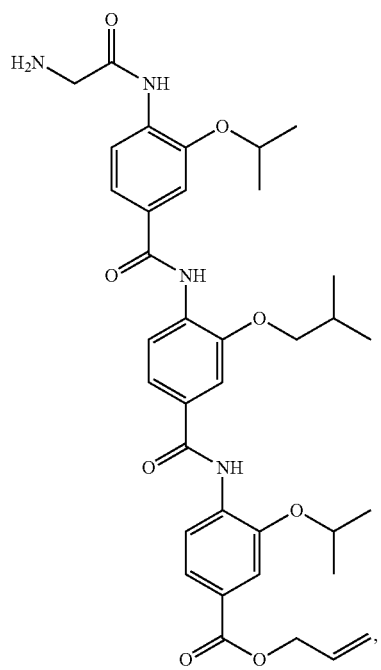
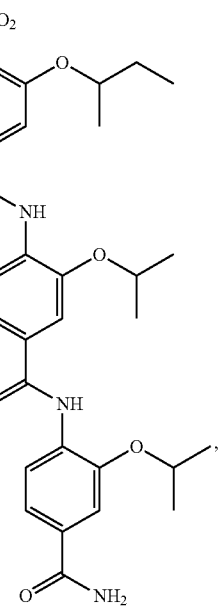

37
-continued
38
-continued
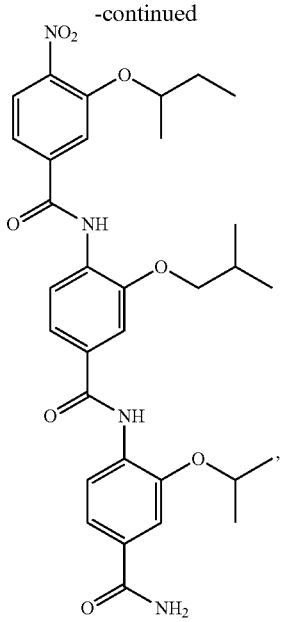
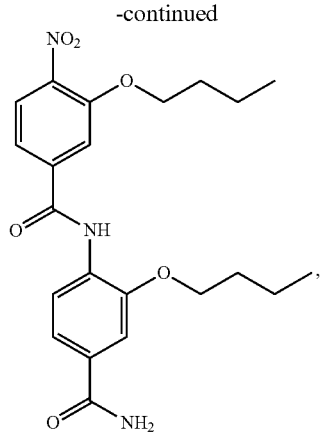
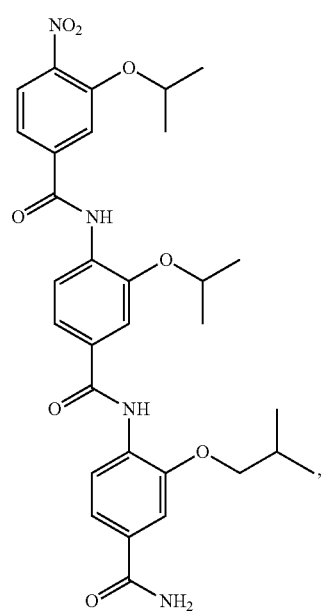
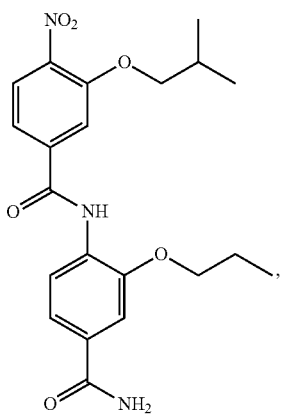

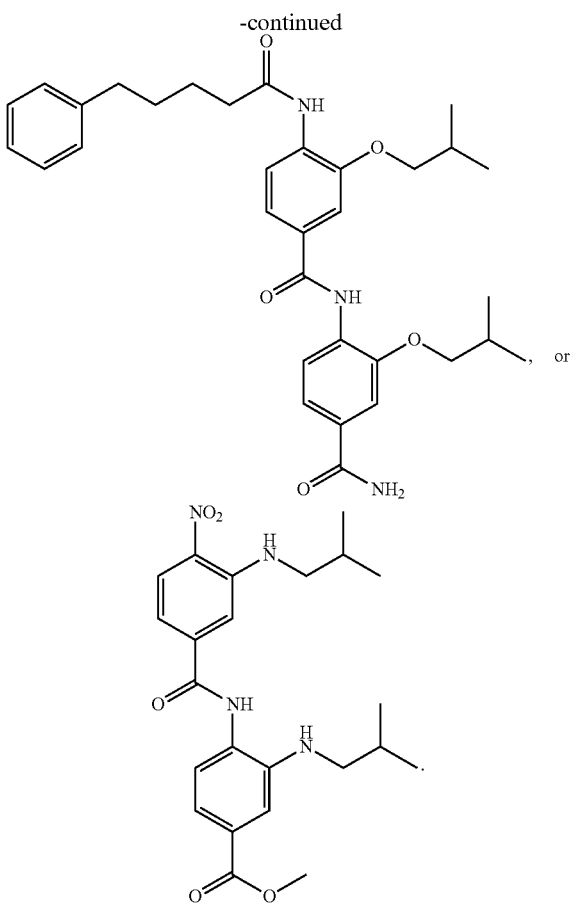

21. The method of claim 1, wherein the tumor cell is an androgen receptor (AR)-positive tumor cell.

22. The method of claim 1, wherein the tumor cell is an estrogen receptor (ER)-positive tumor cell.

23. The method of claim 1, tumor cell is a carcinoma cell.

24. The method of claim 23, wherein the carcinoma cell is a breast carcinoma cell.

25. The method of claim 1, wherein the breast cancer cell is a triple-negative breast cancer cell.

26. The method of claim 1, wherein the tumor cell is a brain cancer cell.

27. The method of claim 25, wherein the brain cancer cell is a glioma.

28. The method of claim 1, wherein the tumor cell is an ovarian cancer cell.

29. The method of claim 1, wherein administering comprises local, regional, systemic, or continual administration.

30. The method of claim 1, wherein said peptidomimetic compound is fused to a cell delivery domain.

31. The method of claim 1, wherein inhibiting comprises inducing growth arrest of said tumor cell, apoptosis of said tumor cell and/or necrosis of a tumor tissue comprising said tumor cell.

32. The method of claim 1, further comprising providing to said subject a second anti-cancer therapy.

33. The method of claim 32, wherein said second anti-cancer therapy is surgery, chemotherapy, radiotherapy, hormonal therapy, toxin therapy, immunotherapy, and cryotherapy.

34. The method of claim 32, wherein said second anti-cancer therapy is provided prior to administering said compound.

35. The method of claim 32, wherein said second anti-cancer therapy is provided after administering said compound.

36. The method of claim 32, wherein said second anti-cancer therapy is provided at the same time as said compound.

37. The method of claim 1, wherein said subject is a human.

38. The method of claim 1, wherein said compound is administered at about 0.1 to about 100 mg/kg.

39. The method of claim 38, wherein said compound is administered at about 1 to about 50 mg/kg.

40. The method of claim 1, wherein said compound is administered daily.

41. The method of claim 40, wherein said compound is administered daily for 7 days, 2 weeks, 3 weeks, 4 weeks, one month, 6 weeks, 8 weeks, two months, 12 weeks, or 3 months.

42. The method of claim 1, wherein said compound is administered weekly.

43. The method of claim 42, wherein said compound is administered weekly for 2 weeks, 3 weeks, 4 weeks, 6 weeks, 8 weeks, 10 weeks, or 12 weeks.

44. The method of claim 1, further comprising assessing AR- or ER-driven gene expression in said tumor cell of said subject prior to administering said compound.

45. The method of claim 1, further comprising assessing AR- or ER-driven gene expression in said tumor cell of said subject after administering said compound.

* * * * *